United States Patent [19]

Bhatnagar

[11] Patent Number: 5,583,128

[45] Date of Patent: Dec. 10, 1996

[54] CONTRACEPTION IN FEMALE PRIMATES WITHOUT AFFECTING THE MENSTRUAL CYCLE

[75] Inventor: Ajay Bhatnagar, Basel, Switzerland

[73] Assignee: Ciba-Geigy Corporation, Tarrytown, N.Y.

[21] Appl. No.: 300,668

[22] Filed: Sep. 2, 1994

Related U.S. Application Data

[63] Continuation of Ser. No. 195,892, Feb. 10, 1994, abandoned, which is a continuation of Ser. No. 872,272, Apr. 22, 1992, abandoned.

[30] Foreign Application Priority Data

Apr. 24, 1991 [CH] Switzerland .............................. 1227/91

[51] Int. Cl.$^6$ ...................... A61K 31/56; A61K 31/495; A61K 31/505; A61K 31/435; A61K 31/44; A61K 31/41; A61K 31/425; A61K 31/42; A61K 31/415; A61K 31/34

[52] U.S. Cl. ........................ 514/177; 514/255; 514/256; 514/277; 514/299; 514/300; 514/361; 514/362; 514/363; 514/364; 514/372; 514/374; 514/378; 514/381; 514/383; 514/384; 514/393; 514/394; 514/396; 514/401; 514/469; 514/843

[58] Field of Search ...................... 514/300, 843, 514/177, 255, 256, 277, 299, 300, 361, 362, 363, 364, 372, 374, 378, 381, 383, 384, 393, 394, 396, 401, 469, 843

[56] References Cited

U.S. PATENT DOCUMENTS

| | | | |
|---|---|---|---|
| 4,289,762 | 9/1981 | Metcalf et al. | 260/397.4 |
| 4,322,416 | 3/1982 | Metcalf et al. | 424/242 |
| 4,617,307 | 10/1986 | Browne | 514/300 |
| 4,677,129 | 6/1987 | Alder et al. | 514/299 |
| 4,728,645 | 3/1988 | Browne | 514/214 |
| 4,749,713 | 6/1988 | Bowman et al. | 514/341 |
| 4,808,616 | 2/1989 | Buzzetti | 514/177 |
| 4,839,379 | 6/1989 | Stanek et al. | 514/421 |
| 4,857,660 | 8/1989 | Alder et al. | 562/435 |
| 4,889,861 | 12/1989 | Browne | 514/300 |
| 4,904,650 | 2/1990 | Buzzetti et al. | 514/177 |
| 4,910,212 | 3/1990 | Boyle et al. | 514/383 |
| 4,937,250 | 6/1990 | Bowman et al. | 514/341 |
| 4,978,672 | 12/1990 | Bowman et al. | 514/383 |
| 5,002,940 | 3/1991 | Geller et al. | 514/178 |
| 5,057,521 | 10/1991 | Hausler et al. | 514/300 |
| 5,071,861 | 12/1991 | Bowman et al. | 514/332 |
| 5,073,574 | 12/1991 | Lang | 514/381 |
| 5,098,911 | 3/1992 | Ibrahim | 514/300 |
| 5,112,845 | 6/1992 | Bowman et al. | 514/399 |
| 5,352,795 | 10/1994 | Bowman et al. | 548/262.2 |

FOREIGN PATENT DOCUMENTS

| | | |
|---|---|---|
| 0116329 | 8/1984 | European Pat. Off. . |
| 0227472 | 7/1987 | European Pat. Off. . |
| 0250262 | 12/1987 | European Pat. Off. . |
| 0250198 | 12/1987 | European Pat. Off. . |
| 0253591 | 1/1988 | European Pat. Off. . |
| 0265119 | 4/1988 | European Pat. Off. . |
| 0276122 | 7/1988 | European Pat. Off. . |
| 0286578 | 10/1988 | European Pat. Off. . |
| 0289450 | 11/1988 | European Pat. Off. . |
| 0289451 | 11/1988 | European Pat. Off. . |
| 0296749 | 12/1988 | European Pat. Off. . |
| 0293978 | 12/1988 | European Pat. Off. . |
| 0299683 | 1/1989 | European Pat. Off. . |
| 0299684 | 1/1989 | European Pat. Off. . |
| 0307135 | 3/1989 | European Pat. Off. . |
| 0316097 | 5/1989 | European Pat. Off. . |
| 0337928 | 10/1989 | European Pat. Off. . |
| 0340153 | 11/1989 | European Pat. Off. . |
| 0354683 | 2/1990 | European Pat. Off. . |
| 0354689 | 2/1990 | European Pat. Off. . |
| 0356673 | 3/1990 | European Pat. Off. . |
| 0445073 | 9/1991 | European Pat. Off. . |
| 0457716 | 11/1991 | European Pat. Off. . |
| 0477141 | 3/1992 | European Pat. Off. . |
| 3422187 | 12/1985 | Germany . |
| 3525560 | 1/1987 | Germany . |
| 3539244 | 5/1987 | Germany . |
| 3740125 | 6/1988 | Germany . |
| 3720234 | 12/1988 | Germany . |
| 2171100 | 8/1986 | United Kingdom . |
| 2191198 | 12/1987 | United Kingdom . |
| 2191777 | 12/1987 | United Kingdom . |
| 2222589 | 3/1990 | United Kingdom . |
| 2222401 | 3/1990 | United Kingdom . |

OTHER PUBLICATIONS

Brodie et al.; J. Steroid Biochemistry, 11, 107–112 (1979) "Aromatase Inhibitors and Their Use in Controlling Estrogen Dependent Processes".

Wu et al; J. Reprod. Fert. 66, 655–662 (1982) "Effect of Aromatase Inhibitor on Estrogen Production in Rabbit Blastocytes".

Steele et al; Steroids 50, 147–161 (1986) "In Vitro & In Vivo Studies Demonstrating Potent and Selective Estrogen Inhibition with the non-steroidal Aromatase Inhibitor CGS16949A."

Mead et al; Biology of Reproduction 27, 540–547 (1982). "Is Estrogen Required for Implantation in the Ferret."

Brodie et al; Endocrinology 104, No. 1, 118–121 (1979) "Antifertility Effects of an Aromatase Inhibitor, 1,4,6–Androstatriene–3,17–Dione".

Brodie et al; Biology of Reproduction. 18, 365–370 (1978). "Aromatase Inhibitors III. Studies on the Antifertility Effect of 4–Acetoxy–4–Androstene–3,17–Dione."

(List continued on next page.)

Primary Examiner—Kimberly Jordan
Attorney, Agent, or Firm—Marla J. Mathias; Karen G. Kaiser; Irving M. Fishman

[57] ABSTRACT

The invention relates to the use of aromatase inhibitors for contraception in female primates and to a method for contraception in female primates using such substances and to the use of those substances for the preparation of pharmaceutical compositions for contraception in female primates.

20 Claims, No Drawings

OTHER PUBLICATIONS

Brodie et al; Endocrinology 100: 1684–1695. "The Effect of an Aromatase Inhibitor, 4–hydroxy–4–Androstene–3, 17–Dione on Estrogen Dependent Processes in Reproduction and Brest Cancer." (1975).

Mead et al. Biology of Reproduction 22, 560–565 (1980) "Aromatase Activity in the *Corpora Lutea* of the Ferret."

Moudgal et al; Biology of Reproduction 1991 (Abstract) "Contraceptive Efficacy of an Aromatase Inhibitor (CGS 16949A) as analyzed in the Bonnet Monkey."

Gosh et al; Biology of Reproduction 40, Suppl. 1, 122. "Effect of an Aromatase Inhibitor (4–hydroxyandrostenedione) in Pre–Implantation Hamster Embryos" (1989).

Derwent Abstract of EP 277910; Aug. 1988.

CONTRACEPTION IN FEMALE PRIMATES WITHOUT AFFECTING THE MENSTRUAL CYCLE

This is a continuation of Ser. No. 08/195,892, filed Feb. 10, 1994, abandoned, which is a continuation of Ser. No. 07/872,272, filed Apr. 22, 1992, abandoned.

Pregnancy occurs in primates, including humans, when a fertilised egg has become implanted in the mucous coat of the uterus. In the course of the female cycle, under the control of the anterior pituitary hormones FSH and LH, follicle stimulation and ovulation occur, whereupon the ovum is released into the funnel of the fallopian tube. If a sperm cell meets the ovum, fertilisation occurs. The fertilised egg takes 3–4 days to pass through the fallopian tube and into the uterus. During that time, by a series of divisions, it develops into a blastocyst, which implants in the tissue of the uterus approximately 7 days after fertilisation.

Conventional hormonal contraception (the "pill") relies on the inhibition of ovulation. The compositions used are a combination of synthetic gestagens and oestrogens which, by means of a negative feed-back mechanism, inhibit secretion of the gonadotropic hormones LH and FSH and thus inhibit follicle stimulation and ovulation.

The so-called "minipill" consists of a low dose of gestagen. Contraceptives of that type do not have an inhibiting effect on the cycle, rather they stimulate the production of cervical mucus and alter its physical properties so that the sperm are not able to pass through it. This form of contraception relies exclusively on a mechanical barrier produced by physically altering the cervical mucus and is therefore less reliable than the ingestion of ovulation inhibitors, but on the other hand is associated with fewer risks (side effects).

It would be very desirable to be able to combine the advantages of the "pill"—large degree of reliability—with those of the "minipill"—no effect on the female cycle.

It has now been found that it is possible, surprisingly, by administering aromatase inhibitors to female primates, including humans, to effect reliable contraception without at the same time substantially affecting the menstrual cycle of the female primate.

Substances that inhibit the enzyme aromatase are already known. Furthermore, aromatase inhibitors have already been proposed as anti-fertility agents for women of reproductive age (see, for example, EP-A-340 153, page 3, lines 5–6). In all of those cases, however, the aromatase inhibitor is intended to reduce the oestrogen level of the female mammal in such a manner that ovulation as well as implantation is suppressed. It goes without saying that, just as in the case of the conventional "pill", the female cycle is greatly affected by this.

In contrast, the present invention relates to the use of aromatase inhibitors for contraception in female primates of reproductive age without substantially affecting the menstrual cycle of the female primate. The contraceptive action of the aromatase inhibitors is reversible, that is to say once their use has been discontinued pregnancy can occur in the treated primates as early as the next cycle.

For the purpose of contraception, the maximum dose of aromatase inhibitor administered is one that has substantially no effect on the menstrual cycle of the female primate.

The invention relates to the use of aromatase inhibitors for contraception in female primates of reproductive age in a dose at which the menstrual cycle of the female primate remains substantially unaffected.

The absolute upper limit for the daily doses required for contraceptive action depends entirely on the type of aromatase inhibitor that is used. In the case of the highly active aromatase inhibitors that can be used according to the invention, the daily doses are generally from approximately 0.05 mg to approximately 30 mg, based on an individual having a body weight of approximately 60 kg, preference being given to the administration of individual doses of from approximately 0.01 mg to approximately 20 mg. In the case of less active aromatase inhibitors the daily doses can, however, be higher.

The invention relates also to a method of contraception in female primates of reproductive age which comprises administering aromatase inhibitors to the female primate in a dose at which the menstrual cycle of the female primate remains substantially unaffected.

The invention relates further to the use of aromatase inhibitors for the preparation of pharmaceutical compositions that comprise the aromatase inhibitors in a dose that prevents conception in female primates of reproductive age without substantially affecting the menstrual cycle of the female primate, which means that the menstrual cycle proceeds substantially as it would without the administration of the aromatase inhibitors. There is no substantial disruption of the cycle or delay in or bringing forward of menstruation caused by the administration of the aromatase inhibitor.

In accordance with the customary definition, "primates" are to be understood as being prosimians, apes and humans. Female primates are distinguished by the fact that they all have a very similar reproductive endocrinology which is very different from that of other mammals, for example of rodents.

The contraceptive action according to the invention of aromatase inhibitors in primates can be determined, for example, by means of the following experimental procedure:

Female apes in the fertile phase of the cycle are cohabited with male members of the same species that have proved to be fertile. After ovulation the female animals are treated with an aromatase inhibitor. Under the same experimental conditions a control not treated with the test compound is carried out and the incidence of pregnancy in the treatment group is compared with that in the untreated control group. In order to assess the regularity of the cycle, suitable parameters, for example basal temperature, hormone levels, such as serum hormone levels, especially the serum progesterone level, and/or the onset of menstruation at the expected time are measured throughout the experiment. In addition, parameters of the subsequent cycle, for example the onset of menstruation, the length of the luteal phase and/or follicle function can be used to demonstrate that the menstrual cycle of the primates treated with an aromatase inhibitor used in accordance with the invention remains substantially unaffected. With the use according to the invention of the aromatase inhibitors, no pregnancy occurs in the treated primates, and the menstrual cycle proceeds with essentially the customary regularity (i.e. essentially as without the administration of aromatase inhibitors), which is evident, for example, from the fact that menstruation occurs at the expected time and that the length of the cycle, the length of the luteal phase, the progesterone profile and/or follicle function in the subsequent cycle remain substantially unaffected.

The minimum effective dose of an aromatase inhibitor required for the use according to the invention can be determined experimentally, for example in apes, for example using the following experimental procedures:

a) the overall dose of administered aromatase inhibitor is reduced until no contraceptive action is observed, i.e. until a significant proportion of the animals become pregnant; and/or b) the duration of treatment is reduced until no contraceptive action is observed, i.e. until a significant proportion of the animals or all the animals become pregnant.

The minimum dose is defined as the lowest dose of active ingredient that leads to a significant reduction in the incidence of pregnancy as compared with the untreated control.

Significant means significant in accordance with current statistical methods, for example Student's t-test.

The duration of administration of the aromatase inhibitors used in accordance with the invention shall be selected so that the menstrual cycle of the female primate is substantially unaffected. For example, administration may begin after ovulation, for example two to three days after ovulation, and may continue for a period of from approximately five or six days to approximately the end of the cycle.

By "aromatase inhibitors" there are to be understood substances that inhibit the enzyme aromatase (=oestrogen synthetase), which is responsible for converting androgens to oestrogens. Within the context of the present invention, preference is given to selective aromatase inhibitors, i.e. those that, apart from inhibiting aromatase, exhibit as few other, undesired inhibiting effects as possible on the biosynthesis of other steroid hormones, such as gestagens, androgens and gluco- and mineralo-corticoids, and that, for example, do not induce adrenal hypertrophy.

Aromatase inhibitors may have a non-steroidal or a steroidal chemical structure. According to the present invention, both non-steroidal aromatase inhibitors and steroidal aromatase inhibitors can be used.

By aromatase inhibitors there are to be understood especially those substances that in a determination of the in vitro inhibition of aromatase activity exhibit $IC_{50}$ values of $10^{-5}$M or lower, especially $10^{-6}$M or lower, preferably $10^{-7}$M or lower and most especially $10^{-8}$M or lower.

The in vitro inhibition of aromatase activity can be demonstrated, for example, using the methods described in J. Biol. Chem. 249, 5364 (1974) or in J. Enzyme Inhib. 4, 169 (1990). In addition, $IC_{50}$ values for aromatase inhibition can be obtained, for example, in vitro by a direct product isolation method relating to inhibition of the conversion of 4-$^{14}$C-androstenedione to 4-$^{14}$C-oestrone in human placental microsomes.

By aromatase inhibitors there are to be understood most especially substances for which the minimum effective dose in the case of in vivo aromatase inhibition is 10 mg/kg or less, especially 1 mg/kg or less, preferably 0.1 mg/kg or less and most especially 0.01 mg/kg or less.

In vivo aromatase inhibition can be determined, for example, by the following method [see J. Enzyme Inhib. 4, 179 (1990)]: androstenedione (30 mg/kg subcutaneously) is administered on its own or together with a compound of the invention (orally or subcutaneously) to sexually immature female rats for a period of 4 days. After the fourth administration, the rats are sacrificed and the uteri are isolated and weighed. The aromatase inhibition is determined by the extent to which the hypertrophy of the uterus induced by the administration of androstenedione alone is suppressed or reduced by the simultaneous administration of the compound according to the invention.

The following groups of compounds are listed as examples of aromatase inhibitors. Each individual group forms a group of aromatase inhibitors that can be used successfully in accordance with the present invention:

(a) The compounds of formulae I and I* as defined in EP-A-165 904. These are especially the compounds of formula I

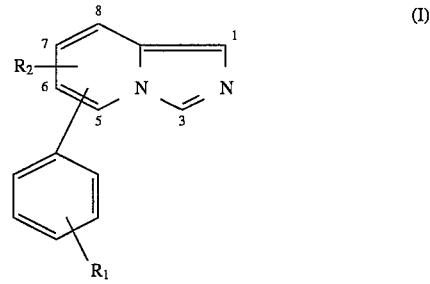

wherein $R_1$ is hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or by cyano; nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, N-thiomorpholino, N-piperazino that is unsubstituted or lower alkyl-substituted in the 4-position, tri-lower alkylammonio, sulfo, lower alkoxysulfonyl, sulfamoyl, lower alkylsulfamoyl, di-lower alkylsulfamoyl, formyl; iminomethyl that is unsubstituted or substituted at the nitrogen atom by hydroxy, lower alkoxy, lower alkanoyloxy, lower alkyl, phenyl or by amino; $C_2$-$C_7$alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl; the 7,8-dihydro derivatives thereof; and the compounds of formula I*

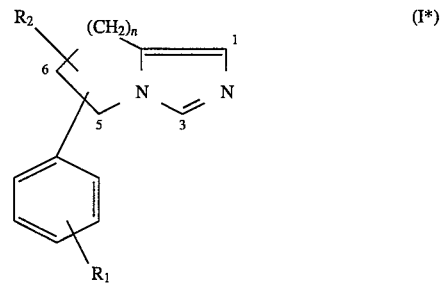

wherein n is 0, 1, 2, 3 or 4; and $R_1$ and $R_2$ are as defined above for formula I; it being possible for the phenyl ring in the radicals phenylsulfonyloxy, phenyliminomethyl, benzoyl, phenyl-lower alkyl, phenyl-lower alkylthio and phenylthio to be unsubstituted or substituted by lower alkyl, lower alkoxy or by halogen; it being possible in a compound of formula I* for the two substituents $C_6H_4$—$R_1$ and $R_2$ to be linked to each of the saturated carbon atoms of the saturated ring, either both to the same carbon atom or both to different carbon atoms, and pharmaceutically acceptable salts thereof.

Individual compounds that may be given special mention here are:

(1) 5-(p-cyanophenyl)imidazo[1,5-a]pyridine,
(2) 5-(p-ethoxycarbonylphenyl)imidazo[1,5-a]pyridine, (3) 5-(p-carboxyphenyl)imidazo[1,5-a]pyridine,
(4) 5-(p-tert-butylaminocarbonylphenyl)imidazo[1,5-a]pyridine,
(5) 5-(p-ethoxycarbonylphenyl)-5,6,7,8-tetrahydroimidazo[1,5-a]pyridine,
(6) 5-(p-carboxyphenyl)-5,6,7,8-tetrahydroimidazo[1,5-a]pyridine,
(7) 5-(p-carbamoylphenyl)-5,6,7,8-tetrahydroimidazo[1,5-a]pyridine,
(8) 5-(p-tolyl)-5,6,7,8-tetrahydroimidazo[1,5-a]pyridine,
(9) 5-(p-hydroxymethylphenyl)imidazo[1,5-a]pyridine,
(10) 5-(p-cyanophenyl)-7,8-dihydroimidazo[1,5-a]pyridine,
(11) 5-(p-bromophenyl)-5,6,7,8-tetrahydroimidazo[1,5-a]pyridine,
(12) 5-(p-hydroxymethylphenyl)-5,6,7,8-tetrahydroimidazo[1,5-a]pyridine,
(13) 5-(p-formylphenyl)-5,6,7,8-tetrahydroimidazo[1,5-a]pyridine,
(14) 5-(p-cyanophenyl)-5-methylthio-5,6,7,8-tetrahydroimidazo[1,5-a]pyridine,
(15) 5-(p-cyanophenyl)-5-ethoxycarbonyl-5,6,7,8-tetrahydroimidazo[1,5-a]pyridine,
(16) 5-(p-aminophenyl)-5,6,7,8-tetrahydroimidazo[1,5-a]pyridine,
(17) 5-(p-formylphenyl)imidazo[1,5-a]pyridine,
(18) 5-(p-carbamoylphenyl)imidazo[1,5-a]pyridine,
(19) 5H-5-(4-tert-butylaminocarbonylphenyl)-6,7-dihydropyrrolo[1,2-c]imidazole,
(20) 5H-5-(4-cyanophenyl)-6,7-dihydropyrrolo[1,2-c]imidazole,
(21) 5H-5-(4-cyanophenyl)-6,7,8,9-tetrahydroimidazo[1,5-a]azepine,
(22) 5-(4-cyanophenyl)-6-ethoxycarbonylmethyl-5,6,7,8-tetrahydroimidazo[1,5-a]pyridine,
(23) 5-(4-cyanophenyl)-6-carboxymethyl-5,6,7,8-tetrahydroimidazo[1,5-a]pyridine,
(24) 5-benzyl-5-(4-cyanophenyl)-5,6,7,8-tetrahydroimidazo[1,5-a]pyridine,
(25) 7-(p-cyanophenyl)-5,6,7,8-tetrahydroimidazo[1,5-a]pyridine,
(26) 7-(p-carbamoylphenyl)-5,6,7,8-tetrahydroimidazo[1,5-a]pyridine,
(27) 5-(p-cyanophenyl)-5,6,7,8-tetrahydroimidazo[1,5-a]pyridine (=Fadrozol).

(b) The compounds of formula I as defined in EP-A 236 940. These are especially the compounds of formula I

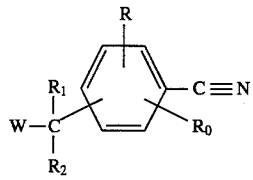

wherein R and $R_0$, independently of one another, are each hydrogen or lower alkyl, or R and $R_0$ at adjacent carbon atoms, together with the benzene ring to which they are bonded, form a naphthalene or tetrahydronaphthalene ring; wherein $R_1$ is hydrogen, lower alkyl, aryl, aryl-lower alkyl or lower alkenyl; $R_2$ is hydrogen, lower alkyl, aryl, aryl-lower alkyl, (lower alkyl, aryl or aryl-lower alkyl)-thio or lower alkenyl, or wherein $R_1$ and $R_2$ together are lower alkylidene or $C_4$–$C_6$alkylene; wherein W is 1-imidazolyl, 1-(1,2,4 or 1,3,4)-triazolyl, 3-pyridyl or one of the mentioned heterocyclic radicals substituted by lower alkyl; and aryl within the context of the above definitions has the following meanings: phenyl that is unsubstituted or substituted by one or two substituents from the group lower alkyl, lower alkoxy, hydroxy, lower alkanoyloxy, nitro, amino, halogen, trifluoromethyl, cyano, carboxy, lower alkoxycarbonyl, carbamoyl, N-lower alkylcarbamoyl, N,N-di-lower alkylcarbamoyl, lower alkanoyl, benzoyl, lower alkylsulfonyl, sulfamoyl, N-lower alkylsulfamoyl and N,N-di-lower alkylsulfamoyl; also thienyl, indolyl, pyridyl or furyl, or one of the four last-mentioned heterocyclic radicals monosubstituted by lower alkyl, lower alkoxy, cyano or by halogen; and pharmaceutically acceptable salts thereof.

Individual compounds from that group that may be given special mention are:
(1) 4-[alpha-(4-cyanophenyl)-1-imidazolylmethyl]-benzonitrile,
(2) 4-[alpha-(3-pyridyl)-1-imidazolylmethyl]-benzonitrile,
(3) 4-[alpha-(4-cyanobenzyl)-1-imidazolylmethyl]-benzonitrile,
(4) 1-(4-cyanophenyl)-1-(1-imidazolyl)-ethylene,
(5) 4-[alpha-(4-cyanophenyl)-1-(1,2,4-triazolyl)methyl]-benzonitrile,
(6) 4-[alpha-(4-cyanophenyl)-3-pyridylmethyl]-benzonitrile.

(c) The compounds of formula I as defined in EP-A-408 509. These are especially the compounds of formula I

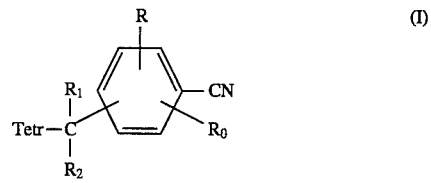

wherein Tetr is 1- or 2-tetrazolyl that is unsubstituted or substituted in the 5-position by lower alkyl, phenyl-lower alkyl or by lower alkanoyl; R and $R_2$, independently of one another, are each hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, heteroaryl, aryl-lower alkyl, $C_3$–$C_6$cycloalkyl, $C_3$–$C_6$cycloalkyl-lower alkyl, lower alkylthio, arylthio or aryl-lower alkylthio; or $R_1$ and $R_2$ together are straight-chained $C_4$–$C_6$alkylene that is unsubstituted or substituted by lower alkyl, or are a group —(CH$_2$)$_m$-1,2-phenylene-(CH$_2$)$_n$— wherein m and n, independently of one another, are each 1 or 2 and 1,2-phenylene is unsubstituted or substituted in the same way as phenyl in the definition of aryl below, or are lower alkylidene that is unsubstituted or mono- or di-substituted by aryl; and R and $R_0$, independently of one another, are each hydrogen or lower alkyl; or R and $R_0$ together, located at adjacent carbon atoms of the benzene ring, are a benzo group that is unsubstituted or substituted in the same way as phenyl in the definition of aryl below; aryl in the above definitions being phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; heteroaryl in the above definitions being an aromatic heterocyclic radical from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl that is unsubstituted or substituted in the same way as phenyl in the definition of aryl above; and pharmaceutically acceptable salts thereof.

Individual compounds from that group that may be given special mention are:
(1) 4-(2-tetrazolyl)methyl-benzonitrile,
(2) 4-[α-(4-cyanophenyl)-(2-tetrazolyl)methyl]-benzonitrile,
(3) 1-cyano-4-(1-tetrazolyl)methyl-naphthalene,
(4) 4-[α-(4-cyanophenyl)-(1-tetrazolyl)methyl]-benzonitrile.

(d) The compounds of formula I as defined in European Patent Application No. 91810110.6. These are especially the compounds of formula I

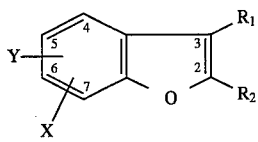

wherein X is halogen, cyano, carbamoyl, N-lower alkylcarbamoyl, N-cycloalkyl-lower alkylcarbamoyl, N,N-di-lower alkylcarbamoyl, N-arylcarbamoyl, hydroxy, lower alkoxy, aryl-lower alkoxy or aryloxy, wherein aryl is phenyl or naphthyl, each of which is unsubstituted or substituted by lower alkyl, hydroxy, lower alkoxy, halogen and/or by trifluoromethyl; Y is a group —CH$_2$—A wherein A is 1-imidazolyl, 1-(1,2,4-triazolyl), 1-(1,3,4-triazolyl), 1-(1,2,3-triazolyl), 1-(1,2,5-triazolyl), 1-tetrazolyl or 2-tetrazolyl, or Y is hydrogen, R$_1$ and R$_2$, independently of one another, are each hydrogen, lower alkyl or a group —CH$_2$—A as defined for Y, or R$_1$ and R$_2$ together are —(CH$_2$)$_n$— wherein n is 3, 4 or 5, with the proviso that one of the radicals Y, R$_1$ and R$_2$ is a group —CH$_2$—A, with the further proviso that in a group —CH$_2$—A as a meaning of R$_1$ or R$_2$, A is other than 1-imidazolyl when X is bromine, cyano or carbamoyl, and with the proviso that in a group —CH$_2$—A as a meaning of Y, A is other than 1-imidazolyl when X is halogen or lower alkoxy, R$_1$ is hydrogen and R$_2$ is hydrogen or lower alkyl, and pharmaceutically acceptable salts thereof.

Individual compounds from that group that may be given special mention are:
(1) 7-cyano-4-[1-(1,2,4-triazolyl)methyl]-2,3-dimethylbenzofuran,
(2) 7-cyano-4-(1-imidazolylmethyl)-2,3-dimethylbenzofuran,
(3) 7-carbamoyl-4-(1-imidazolylmethyl)-2,3-dimethylbenzofuran,
(4) 7-N-(cyclohexylmethyl)carbamoyl-4-(1-imidazolylmethyl)-2,3-dimethylbenzofuran.

(e) The compounds of formula I as defined in Swiss Patent Application 1339/90-7. These are especially the compounds of formula I

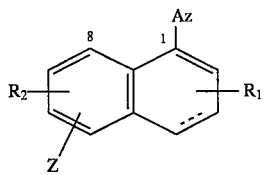

wherein the dotted line denotes an additional bond or no additional bond, Az is imidazolyl, triazolyl or tetrazolyl bonded via a ring nitrogen atom, each of those radicals being unsubstituted or substituted at carbon atoms by lower alkyl or by aryl-lower alkyl, Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl, and R$_1$ and R$_2$, independently of one another, are each hydrogen, lower alkyl, lower alkoxy, hydroxy, halogen or trifluoromethyl; aryl being phenyl or naphthyl each of which is unsubstituted or substituted by one or two substituents from the group consisting of lower alkyl, lower alkoxy, hydroxy, halogen and trifluoromethyl; with the proviso that neither Z nor R$_2$ is hydroxy in the 8-position, and pharmaceutically acceptable salts thereof.

Individual compounds from that group that may be given special mention are:
(1) 6-cyano-1-(1-imidazolyl)-3,4-dihydronaphthalene,
(2) 6-cyano-1-[1-(1,2,4-triazolyl)]-3,4-dihydronaphthalene,
(3) 6-chloro-1-(1-imidazolyl)-3,4-dihydronaphthalene,
(4) 6-bromo-1-(1-imidazolyl)-3,4-dihydronaphthalene.

(f) The compounds of formula I as defined in Swiss Patent Application 3014/90-0. These are especially the compounds of formula I

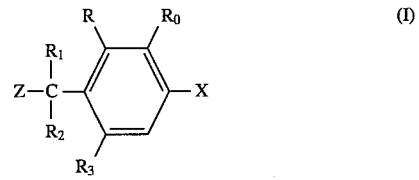

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl), 5-(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and R$_0$ are hydrogen; or R and R$_0$ together are a benzo group that is unsubstituted or substituted by lower alkyl, lower alkoxy, hydroxy, halogen or by trifluoromethyl; R$_1$ is hydrogen, hydroxy, chlorine or fluorine; R$_3$ is hydrogen; R$_2$ is hydrogen, lower alkyl or phenyl that is unsubstituted or substituted by lower alkyl, lower alkoxy, hydroxy, halogen, trifluoromethyl or by cyano; or R$_1$ and R$_2$ together are methylidene; or R$_2$ and R$_3$ together are —(CH$_2$)$_3$—; or R$_1$ and R$_2$ and R$_3$ together are a group =CH—(CH$_2$)$_2$— wherein the single bone is linked to the benzene ring; X is cyano; and X may also be halogen when R$_2$ and R$_3$ together are —(CH$_2$)$_3$— or R$_1$ and R$_2$ and R$_3$ together are a group =CH—(CH$_2$)$_2$—; and pharmaceutically acceptable salts thereof.

Individual compounds from that group that may be given special mention are:
(1) 4-[α-(4-cyanophenyl)-α-hydroxy-5-isothiazolylmethyl]- benzonitrile.
(2) 4-[α-(4-cyanophenyl)-5-isothiazolylmethyl]-benzonitrile,
(3) 4-[α-(4-cyanophenyl)-5-thiazolylmethyl]-benzonitrile,
(4) 1-(4-cyanophenyl)-1-(5-thiazolyl)-ethylene,
(5) 6-cyano-1-(5-isothiazolyl)-3,4-dihydronaphthalene,
(6) 6-cyano-1-(5-thiazolyl)-3,4-dihydronaphthalene.

(g) The compounds of formula VI as defined in Swiss Patent Application 3014/90-0. These are especially the compounds of formula VI

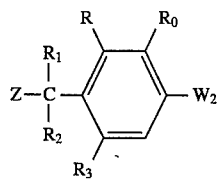

wherein Z is a five-membered nitrogen-containing heteroaromatic ring selected from the group 5-isothiazolyl, 5-thiazolyl, 5-isoxazolyl, 5-oxazolyl, 5-(1,2,3-thiadiazolyl). 5-(1,2,3-oxadiazolyl) 3-(1,2,5-thiadiazolyl), 3-(1,2,5-oxadiazolyl), 4-isothiazolyl. 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl); R and $R_0$ are each hydrogen; or R and $R_0$ together are a benzo group that is unsubstituted or substituted by lower alkyl, lower alkoxy, hydroxy, halogen or by trifluoromethyl; $R_1$ is hydrogen, hydroxy, chlorine or fluorine; $R_3$ is hydrogen; $R2$ is hydrogen, lower alkyl or phenyl that is unsubstituted or substituted by lower alkyl, lower alkoxy, hydroxy, halogen, trifluoromethyl, aryl-lower alkoxy or by aryloxy; or $R_1$ and $R_2$ together are methylidene, and $W_2$ is halogen, hydroxy, lower alkoxy, aryl-lower alkoxy or aryloxy; aryl in each case being phenyl that is unsubstituted or substituted by lower alkyl, lower alkoxy, hydroxy, halogen or by trifluoromethyl; and pharmaceutically acceptable salts thereof.

Individual compounds from that group that may be given special mention are:
(1) bis(4,4'-bromophenyl)-(5-isothiazolyl)methanol,
(2) bis(4,4'-bromophenyl)-(5-isothiazolyl)methane,
(3) bis(4,4'-bromophenyl)-(5-thiazolyl)methanol,
(4) bis(4,4'-bromophenyl)-(5-thiazolyl)methane, (h) The compounds of formula I as defined in Swiss Patent Application 3923/90-4. These are especially the compounds of formula I

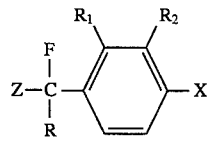

wherein Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidyl, pyrazinyl, pyridazinyl. triazinyl, quinolinyl or isoquinolinyl, all those radicals being bonded via their heterocyclic rings and all those radicals being unsubstituted or substituted by lower alkyl, hydroxy, lower alkoxy, halogen or by trifluoromethyl: $R_1$ and $R_2$, independently of one another, are each hydrogen or lower alkyl; or $R_1$ and $R_2$ together are $C_3$–$C_4$alkylene, or a benzo group that is unsubstituted or substituted as indicated below for aryl; R is hydrogen, lower alkyl, aryl or heteroaryl, and X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, N-hydroxycarbamoyl, hydroxy, lower alkoxy, aryl-lower alkoxy or aryloxy; and wherein X is also halogen when Z is imidazolyl, triazolyl, tetrazolyl, pyrrolyl, pyrazolyl, indolyl, isoindolyl, benzimidazolyl, benzopyrazolyl or benzotriazolyl;

wherein aryl is phenyl or naphthyl, these radicals being unsubstituted or substituted by from 1 to 4 substituents from the group consisting of lower alkyl, lower alkenyl, lower alkynyl, lower alkylene (linked to two adjacent carbon atoms), $C_3$–$C_8$cycloalkyl, phenyl-lower alkyl, phenyl; lower alkyl that is substituted in turn by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenoxy, lower alkenyloxy, halo-lower alkenyloxy, lower alkynyloxy, lower alkylenedioxy (linked to two adjacent carbon atoms), lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, $C_3$–$C_8$cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—, —S— or —NR"— (wherein R" is hydrogen, lower alkyl or lower alkanoyl); lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—, wherein R" is hydrogen, lower alkyl or lower alkanoyl; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-hydroxycarbamoyl, N-phenyl-lower alkylcarbamoyl, N-phenylcarbamoyl, cyano, sulfo, lower alkoxysulfonyl, sulfamoyl, N-lower alkylsulfamoyl, N,N-di-lower alkylsulfamoyl and N-phenylsulfamoyl; the phenyl groups occurring in the substituents of phenyl and naphthyl in turn being unsubstituted or substituted by lower alkyl, lower alkoxy, hydroxy, halogen and/or by trifluoromethyl;

wherein heteroaryl is indolyl, isoindolyl, benzimidazolyl, benzopyrazolyl, benzotriazolyl, benzo[b]furanyl, benzo[b]thienyl, benzoxazolyl or benzothiazolyl, those radicals being unsubstituted or substituted by from 1 to 3 identical or different substituents selected from lower alkyl, hydroxy, lower alkoxy, halogen, cyano and trifluoromethyl; and pharmaceutically acceptable salts thereof.

Those compounds are especially the compounds of formula I whereto Z is 1-imidazolyl, 1-(1,2,4-triazolyl), 1-(1,3,4-triazolyl), 1-(1,2,3-triazolyl), 1-tetrazolyl, 2-tetrazolyl, 3-pyridyl, 4-pyridyl, 4-pyrimidyl, 5-pyrimidinyl or 2-pyrazinyl; $R_1$ and $R_2$, independently of one another, are each hydrogen or lower alkyl; or $R_1$ and $R_2$ together are 1,4-butylene or a benzo group; R is lower alkyl; phenyl that is unsubstituted or substituted by cyano, carbamoyl, halogen, lower alkyl, trifluoromethyl, hydroxy, lower alkoxy or by phenoxy; or benzotriazolyl or benzo[b]furanyl, the last two radicals being unsubstituted or substituted by from 1 to 3 identical or different substituents selected from lower alkyl, halogen and cyano; and X is cyano or carbamoyl; and wherein X is also halogen when Z is 1-imidazolyl, 1-(1,2,4-triazolyl), 1-(1,3,4-triazolyl), 1-(1,2,3-triazolyl), 1-tetrazolyl 2-tetrazolyl; and pharmaceutically acceptable salts thereof.

Individual compounds that may be given special mention here are:
(1) 4-[α-(4-cyanophenyl)-α-fluoro-1-(1,2,4-triazolyl)methyl]-benzonitrile,
(2) 4-[α-(4-cyanophenyl)-α-fluoro-(2-tetrazolyl)methyl]-benzonitrile,
(3) 4-[α-(4-cyanophenyl)-α-fluoro-(1-tetrazolyl)methyl]-benzonitrile,
(4) 4-[α-(4-cyanophenyl)-α-fluoro-(1-imidazolyl)methyl]-benzonitrile,
(5) 1-methyl-6-[α-(4-chlorophenyl)-α-fluoro-1-(1,2,4-triazolyl)methyl]-benzotriazole,
(6) 4-[α-(4-cyanophenyl)-α-fluoro-1-(1,2,3-triazolyl)methyl]-benzonitrile,
(7) 7-cyano-4-[α-(4-cyanophenyl)-α-fluoro-1-(1,2,4-triazolyl)methyl]-2,3-dimethylbenzo[b]furan,
(8) 4-[α-(4-bromophenyl)-α-fluoro-1-(1,2,4-triazolyl)methyl]-benzonitrile,
(9) 4-[α-(4-cyanophenyl)-α-fluoro-(5-pyrimidyl)methyl]-benzonitrile,
(10) 4-[α-(4-bromophenyl)-α-fluoro-(5-pyrimidyl)methyl]-benzonitrile,
(11) 4-[α-(4-cyanophenyl)-α-fluoro-(3-pyridyl)methyl]-benzonitrile,
(12) 7-bromo-4-[α-(4-cyanophenyl)-α-fluoro-(1-imidazolyl)methyl]-2,3-dimethylbenzo[b]furan,
(13) 7-bromo-4-[α-(4-cyanophenyl)-α-fluoro-1-(1,2,4-triazolyl)methyl]-2,3-dimethylbenzo[b]furan,
(14) 4-[α-(4-cyanophenyl)-α-fluoro-(5-pyrimidyl)methyl]-benzonitrile,
(15) 4-[α-(4-bromophenyl)-α-fluoro-(5-pyrimidyl)methyl]-benzonitrile,
(16) 4-[α-(4-cyanophenyl)-1-(1,2,3-triazolyl)methyl]-benzonitrile,
(17) 2,3-dimethyl-4-[α-(4-cyanophenyl)-1-(1,2,4-triazolyl)methyl]-7-cyano-benzo[b]furan,
(18) 4-[α-(4-cyanophenyl)-(5-pyrimidyl)methyl]-benzonitrile,
(19) 4-[α-(4-bromophenyl)-(5-pyrimidyl)methyl]-benzonitrile,
(20) 2,3-dimethyl-4-[α-(4-cyanophenyl)-(1-imidazolyl)methyl]-7-bromo-benzo[b]furan,
(21) 2,3-dimethyl-4-[α-(4-cyanophenyl)-1-(1,2,4-triazolyl)methyl]-7-bromo-benzo-[b]furan.

(i) The compounds of formula I as defined in EP-A-114 033. These are especially the compounds of formula I

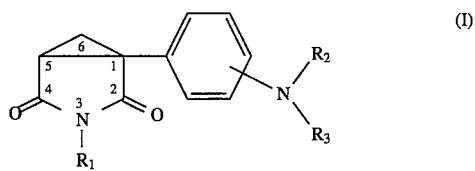

wherein $R_1$ is hydrogen, $R_2$ is hydrogen, sulfo, $C_1$–$C_7$alkanoyl or $C_1$–$C_7$alkanesulfonyl and $R_3$ is hydrogen, or wherein $R_1$ is $C_1$–$C_{12}$alkyl, $C_2$–$C_{12}$alkenyl, $C_2$–$C_7$alkynyl, $C_3$–$C_{10}$cycloalkyl, $C_3$–$C_{10}$cycloalkenyl, $C_3$–$C_6$cycloalkyl-$C_1$–$C_4$alkyl, $C_3$–$C_6$cycloalkyl-$C_2$–$C_4$alkenyl or $C_3$–$C_6$cycloalkenyl-$C_1$–$C_4$alkyl, $R_2$ is hydrogen, $C_1$–$C_7$alkyl, sulfo, $C_1$–$C_7$alkanoyl or $C_1$–$C_7$alkanesulfonyl and $R_3$ is hydrogen or $C_1$–$C_7$alkyl, and salts of those compounds.

Individual compounds from that group that may be given special mention are:
(1) 1-(4-aminophenyl)-3-methyl-3-azabicyclo[3.1.0]hexane-2,4-dione,
(2) 1-(4-aminophenyl)-3-n-propyl-3-azabicyclo[3.1.0]hexane-2,4-dione,
(3) 1-(4-aminophenyl)-3-isobutyl-3-azabicyclo[3.1.0]hexane-2,4-dione,
(4) 1-(4-aminophenyl)-3-n-heptyl-3-azabicyclo[3.1.0]hexane-2,4-dione,
(5) 1-(4-aminophenyl)-3-cyclohexylmethyl-3-azabicyclo[3.1.0]hexane-2,4-dione.

(j) The compounds of formula I as defined in EP-A-166 692. These are especially the compounds of formula I

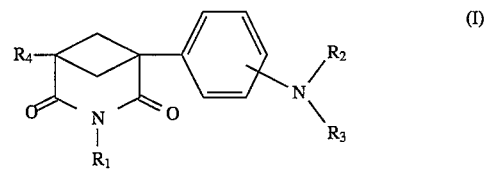

wherein $R_1$ is hydrogen, alkyl having from 1 to 12 carbon atoms, alkenyl having from 2 to 12 carbon atoms, lower alkynyl, cycloalkyl or cycloalkenyl each having from 3 to 10 carbon atoms, cycloalkyl-lower alkyl having from 4 to 10 carbon atoms, cycloalkyl-lower alkenyl having from 5 to 10 carbon atoms, cycloalkenyl-lower alkyl having from 4 to 10 carbon atoms, or aryl having from 6 to 12 carbon atoms or aryl-lower alkyl having from 7 to 15 carbon atoms, each of which is unsubstituted or substituted by lower alkyl, hydroxy, lower alkoxy, acyloxy, amino, lower alkylamino, di-lower alkylamino, acylamino amino or by halogen, $R_2$ is hydrogen, lower alkyl, sulfo, lower alkanoyl or lower alkanesulfonyl, sulfonyl, $R_3$ is hydrogen or lower alkyl and $R_4$ is hydrogen, lower alkyl, phenyl or phenyl substituted by —N($R_2$)($R_3$), and salts thereof, radicals described as "lower" containing up to and including 7 carbon atoms.

Individual compounds from that group that may be given special mention are:
(1) 1-(4-aminophenyl)-3-n-propyl-3-azabicyclo[3.1.1]heptane-2,4-dione,
(2) 1-(4-aminophenyl)-3-methyl-3-azabicyclo[3.1.1]heptane-2,4-dione,
(3) 1-(4-aminophenyl)-3-n-decyl-3-azabicyclo[3.1.1]heptane-2,4-dione,
(4) 1-(4-aminophenyl)-3-cyclohexyl-3-azabicyclo[3.1.1]heptane-2,4-dione,
(5) 1-(4-aminophenyl)-3-cyclohexylmethyl-3-azabicyclo[3.1.1]heptane-2,4-dione.

(k) The compounds of formula I as defined in EP-A-356 673. These are especially the compounds of formula I

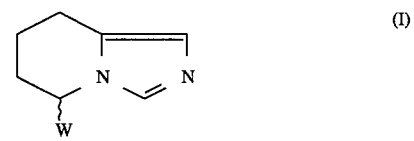

wherein W
(α) is a 2-naphthyl or 1-anthryl radical, wherein each benzene ring is unsubstituted or substituted by a substituent selected from halogen, hydroxy, carboxy, cyano and nitro; or
(β) is 4-pyridyl, 2-pyrimidyl or 2-pyrazinyl, each of those radicals being unsubstituted or substituted by a substituent selected from halogen, cyano, nitro, $C_1$–$C_4$alkoxy and $C_2$–$C_5$alkoxycarbonyl; and pharmaceutically acceptable salts thereof.

Individual compounds from that group that may be given special mention are:
(1) 5-(2'-naphthyl)-5,6,7,8-tetrahydroimidazo[1,5-a]pyridine,
(2) 5-(4'-pyridyl)-5,6,7,8-tetrahydroimidazo[1,5-a]pyridine.

(1) The compounds of formula I or Ia as defined in EP-A-337 929. These are especially the compounds of formula I/Ia

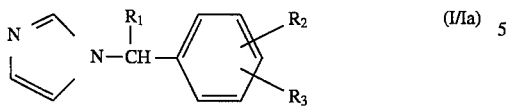

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is benzyloxy, 3-bromo-, 4-bromo-, 4-chloro-, 2,3-, 2,4-, 4,5- or 4,6-dichloro-benzyloxy, and $R_3$ is cyano; $C_2$–$C_{10}$alkanoyl that is unsubstituted or mono- or poly-substituted by halogen, methoxy, amino, hydroxy and/or by cyano; benzoyl that is unsubstituted or substituted by one or more substituents from the group halogen, $C_1$–$C_4$alkyl, methoxy, amino, hydroxy and cyano; carboxy, (methoxy, ethoxy or butoxy)carbonyl, carbamoyl, N-isopropylcarbamoyl, N-phenylcarbamoyl, N-pyrrolidylcarbonyl, nitro or amino; and salts thereof.

Individual compounds from that group that may be given special mention are:
(1) 4-(2,4-dichlorobenzyloxy)-3-[1-(1-imidazolyl)-butyl]-benzonitrile,
(2) (4-(4-bromobenzyloxy)-3-[1-(1-imidazolyl)-butyl]-phenyl pentyl ketone,
(3) 4-(4-bromobenzyloxy)-3-[1-(1-imidazolyl)-butyl]-benzanilide,
(4) 4-(4-bromobenzyloxy)-3-[1-(1-imidazolyl)-butyl]-benzoic acid,
(5) 3-(2,4-dichlorobenzyloxy)-4-[1-(1-imidazolyl)-butyl]-benzonitrile,
(6) 3-(2,4-dichlorobenzyloxy)-4-[1-(1-imidazolyl)-butyl]-benzoic acid methyl ester,
(7) 3-(2,4-dichlorobenzyloxy)-4-[1-(1-imidazolyl)-butyl]-benzoic acid,
(8) 3-(3-bromobenzyloxy)-4-[1-(1-imidazolyl)-butyl]-benzonitrile,
(9) 4-(3-bromobenzyloxy)-3-[1-(1-imidazolyl)-butyl]-benzonitrile,
(10) 3-(4-bromobenzyloxy)-4-[1-(1-imidazolyl)-butyl]-benzoic acid,
(11) 3-(4-bromobenzyloxy)-4-[1-(1-imidazolyl)-butyl]-benzanilide,
(12) 3-(4-bromobenzyloxy)-4-[1-(1-imidazolyl)-butyl]-phenyl pentyl ketone,
(13) 4-(4-bromobenzyloxy)-3-[1-(1-imidazolyl)-butyl]-benzonitrile,
(14) 3-(4-bromobenzyloxy)-4-[1-(1-imidazolyl)-butyl]-benzonitrile,
(15) 4-nitro-2-[1-(1-imidazolyl)-butyl]-phenyl-(2,4-dichlorobenzyl) ether,
(16) 4-amino-2-[1-(1-imidazolyl)-butyl]-phenyl-(2,4-dichlorobenzyl) ether,
(17) (2,4-dichlorobenzyl)-[2-(1-imidazolyl-methyl)-4-nitrophenyl]ether.

(m) The compounds of formula I as defined in EP-A-337 928. These are especially the compounds of formula I

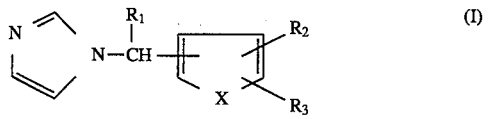

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, $R_2$ is hydrogen, halogen, cyano, methyl, hydroxymethyl, cyanomethyl, methoxymethyl, pyrrolidinylmethyl, carboxy, (methoxy, ethoxy or butoxy)-carbonyl, carbamoyl, N-isopropylcarbamoyl, N-phenylcarbamoyl, N-pyrrolidylcarbonyl; $C_2$–$C_{10}$alkanoyl that is unsubstituted or mono- or poly-substituted by halogen, methoxy, ethoxy, amino, hydroxy and/or by cyano; or benzoyl that is unsubstituted or substituted by one or more substituents from the group halogen, $C_1$–$C_4$alkyl, methoxy, ethoxy, amino, hydroxy and cyano, $R_3$ is hydrogen, benzyloxy, 3-bromo-, 4-bromo-, 4-chloro-, 2,3-, 2,4-, 4,5- or 4,6-dichlorobenzyloxy, and X is —CH=N—; —CH=N(—O)—or —S—; and salts thereof.

Individual compounds from that group that may be given special mention are:
(1) 5-[1-(1-imidazolyl)-butyl]-thiophene-2-carbonitrile,
(2) 2-[1-(1-imidazolyl)-butyl]-thiophene-4-carbonitrile,
(3) 2-[1-(1-imidazolyl)-butyl]-4-bromo-thiophene,
(4) 2-[1-(1-imidazolyl)-butyl]-5-bromo-thiophene,
(5) 5-[1-(1-imidazolyl)-butyl]-2-thienyl pentyl ketone,
(6) 5-[1-(1-imidazolyl)-butyl]-2-thienyl ethyl ketone,
(7) 5-(4-chlorobenzyloxy)-4-[1-(1-imidazolyl)-pentyl]-pyridine-2-carbonitrile,
(8) 3-(4-chlorobenzyloxy)-4-[1-(1-imidazolyl)-pentyl]-pyridine-2-carbonitrile,
(9) 3-(4-chlorobenzyloxy)-4-[1-(1-imidazolyl)-pentyl]-pyridine-N-oxide,
(10) 3-(4-chlorobenzyloxy)-4-[1-(1-imidazolyl)-pentyl]-pyridine.

(n) The compounds of formula I as defined in EP-A-340 153. These are especially the compounds of formula I

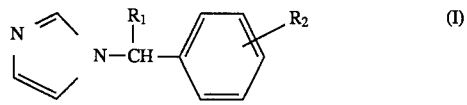

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl, and $R_2$ is a radical from the group methyl, ethyl, propyl, benzyl, phenyl and ethenyl that is substituted by hydroxy, cyano, methoxy, butoxy, phenoxy, amino, pyrrolidinyl, carboxy, lower alkoxycarbonyl or by carbamoyl; or $R_2$ is formyl or derivatised formyl that can be obtained by reaction of the formyl group with an amine or amine derivative from the group hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline; acetyl, propionyl, butyryl, valeryl, caproyl; benzoyl that is unsubstituted or substituted by one or more substituents from the group halogen, $C_1$–$C_4$-alkyl, methoxy, amino, hydroxy and cyano; carboxy, (methoxy, ethoxy or butoxy)carbonyl, carbamoyl, N-isopropylcarbamoyl, N-phenylcarbamoyl or N-pyrrolidylcarbonyl; and salts thereof.

Individual compounds from that group that may be given special mention are:
(1) 4-(1-(1-imidazolyl)-butyl)-benzoic acid methyl ester,
(2) 4-(1-(1-imidazolyl)-butyl)-benzoic acid butyl ester,
(3) 4-(1-(1-imidazolyl)-butyl)-phenyl-acetonitrile,
(4) 4-(1-(1-imidazolyl)-butyl)-benzaldehyde,
(5) 4-(1-(1-imidazolyl)-butyl)-benzyl alcohol,
(6) {4-[1-(1-imidazolyl)-butyl]-phenyl }-2-propyl ketone,
(7) 4-[1-(1-imidazolyl)-butyl]-phenyl propyl ketone,
(8) 4-[1-(1-imidazolyl)-butyl]-phenyl butyl ketone,
(9) 4-[1-(1-imidazolyl)-butyl]-phenyl pentyl ketone,
(10) 4-[1-(1-imidazolyl)-butyl]-phenyl hexyl ketone.

(o) The compounds of formula I as defined in DE-A-4 014 006. These are especially the compounds of formula I

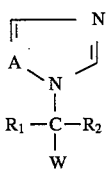

wherein A is an N-atom or a CH radical and W is a radical of the formula

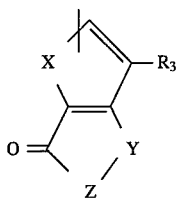

wherein X is an oxygen or a sulfur atom or a —CH=CH— group and Y is a methylene group, an oxygen or a sulfur atom and Z is a —$(CH_2)_n$— group wherein n=1, 2 or 3 and either a) $R_3$ in W is a hydrogen atom and $R_1$ and $R_2$, independently of one another, are each a hydrogen atom, a $C_1$— to $C_{10}$alkyl group or a $C_3$— to $C_7$cycloalkyl group, or b) $R_2$ is as defined under a) and $R_1$ together with $R_3$ forms a —$(CH_2)_m$— group wherein m=2,3,or4, and their pharmaceutically acceptable addition salts with acids.

Individual compounds from that group that may be given special mention are:

(1) 5-[1-(1-imidazolyl)-butyl]-1-indanone, (2) 7-[1-(1-imidazolyl)-butyl]-1-indanone, (3) 6-[1-(1-imidazolyl)-butyl]-1-indanone, (4) 6-(1-imidazolyl)-6,7,8,9-tetrahydro-1H-benz[e]inden-3(2H)-one, (5) 2-[1-(1-imidazolyl)-butyl]-4,5-dihydro-6-oxo-cyclopenta[b]-thiophene, (6) 6-[1-(1-imidazolyl)-butyl]-3,4-dihydro-2H-naphthalen-1-one, (7) 2-[1-(1-imidazolyl)-butyl]-6,7-dihydro-5H-benzo[b]thiophen-4-one, (8) 6-[1-(1-imidazolyl)-butyl]-2H-benzo[b]furan-3-one, (9) 5-[cyclohexyl-(1-imidazolyl)-methyl]-1-indanone,

(10) 2-[1-(1-imidazolyl)-butyl]-4,5-dihydro-6H-benzo[b]thiophen-7-one,

(11) 5-[1-(1-imidazolyl)-1-propyl-butyl]-1-indanone,

(12) 2-[1-(1-imidazolyl)-butyl]-4,5-dihydro-6H-benzo[b]thiophen-7-one,

(13) 2-[1-(1-imidazolyl)-butyl]-4,5-dihydro-6-oxo-cyclopenta[b]-thiophene,

(14) 5-(1-imidazolylmethyl)-1-indanone,

(15) 5-[1-(1,2,4-triazolyl)-methyl]-1-indanone.

(p) The compounds of formula I as disclosed in DE-A-3 926 365. These are especially the compounds of formula I

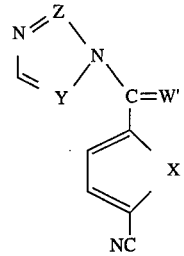

wherein W' is a cyclopentylidene, cyclohexylidene, cycloheptylidene or 2-adamantylidene radical, X is the grouping —CH=CH—, an oxygen or a sulfur atom, and Y and Z, independently of one another, are each a methine group (CH) or a nitrogen atom, and their pharmaceutically acceptable addition salts with acids.

Individual compounds from that group that may be given special mention are:

(1) 4-[1-cyclohexylidene-1-(imidazolyl)-methyl]-benzonitrile, (2) 4-[1-cyclopentylidene-1-(imidazolyl)-methyl]-benzonitrile, (3) 4-[1-cycloheptylidene-1-(imidazolyl)-methyl]-benzonitrile, (4) 4-[2-adamantylidene-1-(imidazolyl)-methyl]-benzonitrile, (5) 4-[1-cyclohexylidene-1-(1,2,4-triazolyl)-methyl]-benzonitrile, (6) 4-[1-cyclopentylidene-1-(1,2,4-triazolyl)-methyl]-benzonitrile, (7) 4-[1-cycloheptylidene-1-(1,2,4-triazolyl)-methyl]-benzonitrile, (8) 4-[2-adamantylidene-1-(1,2,4-triazolyl)-methyl]-benzonitrile, (9) 4-[1-cyclohexylidene-1-(1,2,3-triazolyl)-methyl]-benzonitrile,

(10) 4-[1-cyclopentylidene-1-(1,2,3-triazolyl)-methyl]-benzonitrile,

(11) 5-[cyclohexylidene-1-imidazolylmethyl]-thiophene-2-carbonitrile.

(q) The compounds of formula I as defined in DE-A-3 740 125. These are especially the compounds of formula I

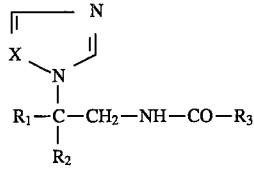

wherein X is CH or N, $R_1$ and $R_2$ are identical or different and are each phenyl or halophenyl, and $R_3$ is $C_1$–$C_4$alkyl; $C_1$–$C_4$alkyl substituted by CN, $C_1$–$C_4$alkoxy, benzyloxy or by $C_1$–$C_4$alkoxy-(mono-, di- or tri-)ethyleneoxy; $C_1$–$C_4$alkoxy, phenyl; phenyl that is substituted by halogen or by cyano; a $C_5$–$C_7$cycloalkyl group that is optionally condensed by benzene, or is thienyl, pyridyl or 2- or 3-indolyl; and acid addition salts thereof.

An individual compound from that group that may be given special mention is:

(1) 2,2-bis(4-chlorophenyl)-2-(1H-imidazol-1-yl)-1-(4-chlorobenzoyl-amino)ethane.

(r) The compounds of formula I as defined in EP-A-293 978. These are especially the compounds of formula I

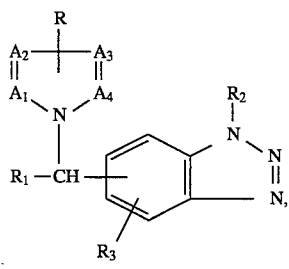

pharmaceutically acceptable salts and stereochemically isomeric forms thereof, wherein $—A_1=A_2—A_3=A_4—$ is a divalent radical selected from —CH=N—CH=CH—, —CH=N—CH=N— and —CH=N—N=CH—, R is hydrogen or $C_1$–$C_6$alkyl; $R_1$ is hydrogen, $C_1$–$C_{10}$alkyl, $C_3$–$C_7$cycloalkyl, $Ar_1$, $Ar_2$–$C_1$–$C_6$alkyl, $C_2$–$C_6$alkenyl or $C_2$–$C_6$alkynyl; $R_2$ is hydrogen; $C_1$–$C_{10}$alkyl that is unsubstituted or substituted by $Ar_1$; $C_3$–$C_7$cycloalkyl, hydroxy, $C_1$–$C_6$alkoxy, $Ar_1$, $C_2$–$C_6$alkenyl, $C_2$–$C_6$alkynyl, $C_3$–$C_7$cycloalkyl, bicyclo[2.2.1]heptan-2-yl, 2,3-dihydro-1H-indenyl, 1,2,3,4-tetrahydronaphthyl, hydroxy; $C_2$–$C_6$alkenyloxy that is unsubstituted or substituted by $Ar_2$; $C_2$–$C_6$alkynyloxy; pyrimidyloxy; di($Ar_2$)methoxy, (1-$C_1$–$C_4$alkyl-4-piperidinyl)oxy, $C_1$–$C_{10}$alkoxy; or $C_1$–$C_{10}$alkoxy that is substituted by halogen, hydroxy, $C_1$–$C_6$alkyloxy, amino, mono- or di-($C_1$–$C_6$alkyl)amino, trifluoromethyl, carboxy, $C_1$–$C_6$alkoxycarbonyl, $Ar_1$, $Ar_2$—O—, $Ar_2$—S—, $C_3$–$C_7$cycloalkyl, 2,3-dihydro-1,4-benzodioxinyl, 1H-benzimidazolyl, $C_1$–$C_4$alkyl-substituted 1H-benzimidazolyl, (1,1'-biphenyl)-4-yl or by 2,3-dihydro-2-oxo-1H-benzimidazolyl; and $R_3$ is hydrogen, nitro, amino, mono- or di-($C_1$–$C_6$alkyl)amino, halogen, $C_1$–$C_6$alkyl, hydroxy or $C_1$–$C_6$alkoxy; wherein $Ar_1$ is phenyl, substituted phenyl, naphthyl, pyridyl, aminopyridyl, imidazolyl, triazolyl, thienyl, halothienyl, furanyl, $C_1$–$C_6$alkylfuranyl, halofuranyl or thiazolyl; wherein $Ar_2$ is phenyl, substituted phenyl or pyridyl; and wherein "substituted phenyl" is phenyl that is substituted by up to 3 substituents in each case selected independently of one another from the group consisting of halogen, hydroxy, hydroxymethyl, trifluoromethyl, $C_1$–$C_6$alkyl, $C_1$–$C_6$alkoxy, $C_1$–$C_6$alkoxycarbonyl, carboxy, formyl, hydroxyiminomethyl, cyano, amino, mono- and di-($C_1$–$C_6$alkyl)amino and nitro.

Individual compounds from that group that may be given special mention are:
(1) 6-[(1H-imidazol-1-yl)-phenylmethyl]-1-methyl-1H-benzotriazole,
(2) 6-[(4-chlorophenyl)(1H-1,2,4-triazol-1-yl)methyl]-1-methyl-1H-benzotriazole.

(s) The compounds of formula II as defined in EP-A-250 198, especially
(1) 2-(4-chlorophenyl)-1,1-di(1,2,4-triazol-1-ylmethyl)ethanol,
(2) 2-(4-fluorophenyl)-1,1-di(1,2,4-triazol-1-ylmethyl)ethanol,
(3) 2-(2-fluoro-4-trifluoromethylphenyl)-1,1-di(1,2,4-triazol-1-ylmethyl)ethanol,
(4) 2-(2,4-dichlorophenyl)-1,1-di(1,2,4-triazol-1-ylmethyl)ethanol,
(5) 2-(4-chlorophenyl)-1,1-di(1,2,4-triazol-1-ylmethyl)-ethanol,
(6) 2-(4-fluorophenyl)-1,1-di(1,2,4-triazol-1-yl-methyl)ethanol.

(t) The compounds of formula I as defined in EP-A-281 283, especially (1) (1R*2R*)-6-fluoro-2-(4-fluorophenyl)-1,2,3,4-tetrahydro-1-(1H-1,2,4-triazol-1-yl-methyl)naphthalene,
(2)(1 R *,2R * )-6-fluoro-2-(4-fluorophenyl )-1,2,3,4-tetrahydro-1-(1H-imidazolylmethyl)-naphthalene,
(3) (1R*,2R*)- and (1R*,2S*)-2-(4-fluorophenyl)-1,2,3,4-tetrahydro-1-(1H-1,2,4-triazol-1-ylmethyl)naphthalene-6-carbonitrile,
(4) (1R*,2R*)- and (1R*,2S*)-2-(4-fluorophenyl)-1,2,3,4-tetrahydro-1-(1H-imidazolylmethyl)naphthalene- 6-carbonitrile,
(5) (1R*,2R*)- and (1R*,2S*)-1,2,3,4-tetrahydro-1-(1H-1,2,4-triazol-1-ylmethyl)-naphthalene-2,6-dicarbonitrile,
(6) (1R*,2R*)- and (1R*,2S*)-1,2,3,4-tetrahydro-1-(1H-imidazol-1-ylmethyl)naphthalene-2,6-dicarbonitrile,
(7) (1R*,2S*)-2-(4-fluorophenyl)-1,2,3,4-tetrahydro-1-(5-methyl-1H-imidazolyl-methyl )naphthalene-6-carbonitrile.

(u) The compounds of formula I as defined in EP-A-296 749, especially
(1) 2,2'-[5-(1H-1,2,4-triazol-1-ylmethyl)-1,3-phenylene] di(2-methylpropiononitrile),
(2) 2,2'-[5-(imidazol-1-ylmethyl)-1,3-phenylene]di(2-methylpropiononitrile), (3) 2-[3-(1-hydroxy-1-methylethyl)-5-(5H-1,2,4-triazol-1-ylmethyl)phenyl]-2-methylpropiononitrile,
(4) 2,2'-[5-dideuterio(1H-1,2,4-triazol-1-yl)methyl-1,3-phenylene]di(2-trideuteriomethyl-3,3,3-trideuteriopropiononitrile),
(5) 2,2'-[5-dideuterio(1H-1,2,4-triazol-1-yl)methyl-3-phenylene]di(2methylpropiononitrile).

(v) The compounds of formula I as defined in EP-A-299 683, especially
(1) (Z)-α-(1,2,4-triazol-1-ylmethyl)stilbene-4,4'-dicarbonitrile,
(2) (Z)-4'-chloro-α-(1,2,4-triazol-1-ylmethyl)stilbene-4-carbonitrile,
(3) (Z)-α-(1,2,4-triazol-1-ylmethyl)-4'-(trifluoromethyl)stilbene-4-carbonitrile,
(4) (E)-β-fluoro-α-(1,2,4-triazol-1-ylmethyl)stilbene-4,4'-dicarbonitrile,
(5) (Z)-4'-fluoro-α-(imidazol-1-ylmethyl)stilbene-4-carbonitrile,
(6) (Z)-2', 4'-dichloro-α-(imidazol-1-ylmethyl)stilbene-4-carbonitrile,
(7) (Z)-4'-chloro-α-(imidazol-1-ylmethyl )stilbene-4-carbonitrile,
(8) (Z)-α-(imidazol-1-ylmethyl)stilbene-4,4'dicarbonitrile,
(9) (Z)-α-(5-methylimidazol-1-ylmethyl)stilbene-4,4'-dicarbonitrile,
(10) (Z)-2-[2-(4-cyanophenyl )-3-(1,2,4-triazol-1-yl)propenyl]pyridine-5-carbonitrile.

(w) The compounds of formula I as defined in EP-A-299 684, especially
(1) 2-(4-chlorobenzyl)-2-fluoro-1,3-di(1,2,4-triazol-1-yl) propane,
(2) 2-fluoro-2-(2-fluoro-4-chlorobenzyl)-1,3-di(1,2,4-triazol-1-yl)propane,
(3) 2-fluoro-2-(2-fluoro-4-trifluoromethylbenzyl)-1,3-di(1, 2,4-triazol-1-yl)propane,
(4) 3-(4-chlorophenyl)-1-(1,2,4-triazol-1-yl)-2-(1,2,4-triazol-1-ylmethyl)butan-2-ol,
(5) 2-(4-chloro-α-fluorobenzyl)-1,3-di(1,2,4-triazol-1-yl) propan-2-ol,
(6) 2-(4-chlorobenzyl)-1,3-bis(1,2,4-triazol-1-yl)propane,
(7) 4-[2-(4-chlorophenyl)-1,3-di(1,2,4-triazol-1-ylmethyl) ethoxymethyl]-benzonitrile,
(8) 1-(4-fluorobenzyl)-2-(2fluoro-4-trifluoromethylphenyl)-1,3-di(1,2,4-triazol-1-yl)-propan-2-ol, (9) 2-(4-chlorophenyl)-1-(4-fluorophenoxy)-1,3-di(1,2,4-triazol-1-yl)propan-2-ol,
(10) 1-(4-cyanobenzyl)-2-(2,4-difluorophenyl)-1,3di(1,2,4-triazol-1-yl)propan-2-ol,
(11) 2-(4-chlorophenyl)-1-phenyl-1,3-di(1,2,4-triazol-1-yl)propan-2-ol.

(x) The compounds as defined in claim 1 of EP-A-316 097, especially
(1) 1,1-dimethyl-8-(1H-1,2,4-triazol-1-ylmethyl)-2(1H)-naphtho[2,1-b]furanone,
(2) 1,2-dihydro 1,1-dimethyl-2-oxo-8-(1H-1,2,4-triazol-1-ylmethyl)naphtho[2,1-b]-furan-7-carbonitrile,
(3) 1,2-dihydro-1,1-dimethyl-2-oxo-8-(1H-1,2,4-triazol-1-ylmethyl)naphtho[2,1-b]-furan-7-carboxamide,
(4) 1,2-dihydro-1,1-dimethyl-2-oxo-8-[di(1H-1,2,4-triazol-1-yl)methyl]naphtho[2,1-b]-furan-7-carbonitrile.

(y) The compounds of formula I as defined in EP-A-354 689, especially
(1) 4-[2-(4-cyanophenyl)-3-(1,2,4-triazol-1-yl)propyl]benzonitrile,
(2) 4-[1-(4-chlorobenzyl)-2-(1,2,4-triazol-1-yl)ethyl]benzonitrile,
(3) 4-[2-(1,2,4-triazol-1-yl)-1-(4-[trifluoromethyl]benzyl)ethyl]benzonitrile,
(4) 4-[2-(1,2,4-triazol-1-yl)-1-(4-[trifluoromethoxy]benzyl)ethyl]benzonitrile.

(z) The compounds of formula (1) as defined in EP-A-354 683, especially
(1) 6-[2-(4-cyanophenyl)-3-(1,2,4-triazol-1-yl)-propyl]nicotinonitrile,
(2) 4-[1-(1,2,4-triazol-1-yl-methyl)-2-(5-[trifluoromethyl]pyrid-2-yl)ethyl]benzonitrile.

Examples of steroidal aromatase inhibitors that may be mentioned are:
(aa) The compounds of formula I as defined in EP-A-181 287. These are especially the compounds of formula I

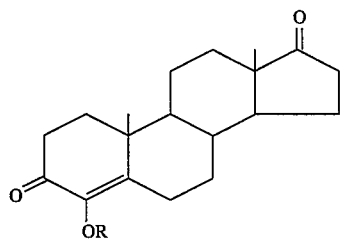

wherein R is hydrogen, acetyl, heptanoyl or benzoyl. An individual compound from that group that may be given special mention is:
(1) 4-hydroxy-4-androstene-3,17-dione.
(ab) The compounds as defined in the claims of U.S. Pat. No. 4,322,416, especially
10-(2-propynyl)-oestr-4-ene-3,17-dione.
(ac) The compounds as defined in the claims of DE-A-3 622 841, especially 6-methyleneandrosta-1,4-diene-3,17-dione.
(ad) The compounds as defined in the claims of GB-A-2 17 1100, especially 4-amino-androsta-1,4,6-triene-3,17-dione.
Also: (ae) androsta-1,4,6-triene-3,17-dione.

The content of the patent applications mentioned under (a) to (z) and (aa) to (ad), especially the subgroups of compounds disclosed therein and the individual compounds disclosed therein as examples, have been incorporated by reference into the disclosure of the present application.

The general terms used hereinbefore and hereinafter to define the compounds have the following meanings:

Organic radicals designated by the term "lower" contain up to and including 7, preferably up to and including 4, carbon atoms.

Acyl is especially lower alkanoyl.

Aryl is, for example, phenyl or 1- or 2-naphthyl, each of which is unsubstituted or substituted by lower alkyl, hydroxy, lower alkoxy, lower alkanoyloxy, amino, lower alkylamino, di-lower alkylamino, lower alkanoylamino or by halogen.

Pharmaceutically acceptable salts of the above-mentioned compounds are, for example, pharmaceutically acceptable acid addition salts or pharmaceutically acceptable metal or ammonium salts.

Pharmaceutically acceptable acid addition salts are especially those with suitable inorganic or organic acids, for example strong mineral acids, such as hydrochloric acid, sulfuric acid or phosphoric acid, or organic acids, especially aliphatic or aromatic carboxylic or sulfonic acids, for example formic, acetic, propionic, succinic, glycolic, lactic, hydroxysuccinic, tartaric, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, gluconic, nicotinic, methanesulfonic, ethanesulfonic, halobenzenesulfonic, p-toluenesulfonic, naphthalenesulfonic, sulfanilic or cyclohexylsulfamic acid; or with other acidic organic substances, for example ascorbic acid. Pharmaceutically acceptable salts may also be formed, for example, with amino acids, such as arginine or lysine.

Compounds containing acid groups, for example a free carboxy or sulfo group, can also form pharmaceutically acceptable metal or ammonium salts, such as alkali metal or alkaline earth metal salts, for example sodium, potassium, magnesium or calcium salts, also ammonium salts derived from ammonia or suitable organic amines. Them come into consideration especially aliphatic, cycloaliphatic, cycloaliphatic-aliphatic or araliphatic primary, secondary or tertiary mono-, di- or poly-amines, such as lower alkylamines, for example di- or tri-ethylamine, hydroxy-lower alkylamines, for example 2-hydroxyethylamine, bis(2-hydroxyethyl)amine or tris(2-hydroxyethyl)amine, basic aliphatic esters or carboxylic acids, for example 4-aminobenzoic acid 2-diethylaminoethyl ester, lower alkyleneamines, for example 1-ethylpiperidine, cycloalkylamines, for example dicyclohexylamine, benzylamines, for example N,N'-dibenzylethylenediamine; also heterocyclic bases, for example of the pyridine type, for example pyridine, collidine or quinoline. If several acidic or basic groups are present, mono- or poly-salts can be formed. Compounds according to the invention having an acidic and a basic group may also be in the form of internal salts, i.e. in the form of zwitterions and another part of the molecule in the form of a normal salt.

In the case of the above-mentioned individual compounds the pharmaceutically acceptable salts are included in each case insofar as the individual compound is capable of salt formation.

The compounds listed, including the individual compounds mentioned, both in free form and in salt form, may also be in the form of hydrates, or their crystals may include, for example, the solvent used for crystallisation. The present invention relates also to all those forms.

Many of the above-mentioned compounds, including the individual compounds mentioned, contain at least one asymmetric carbon atom. They can therefore occur in the form of R- or S-enantiomers and as enantiomeric mixtures thereof, for example in the form of a racemate. The present invention relates to the use of all those forms and to the use of all further isomers, and of mixtures of at least 2 isomers, for example mixtures of diastereoisomers or enantiomers which can occur when there are one or more further asymmetric centres in the molecule. Also included are, for example, all geometric isomers, for example cis- and trans-isomers, that can occur when the compounds contain one or more double bonds.

The invention relates most especially to the use of 5-(p-cyanophenyl)-5,6,7,8-tetrahydroimidazo[1,5-a]pyridine (=Fadrozol), or of a pharmaceutically acceptable acid addition salt thereof, for the purpose of contraception in female primates of reproductive age, without substantially affecting the menstrual cycle of the female primate, and to a method for such contraception in female primates using such compounds, and to the use of those compounds for the preparation of compositions for such contraception in female primates.

The invention relates further to the use of the optical antipodes of the above-mentioned compound, (a) (−)-5-(p-cyanophenyl)-5,6,7,8-tetrahydroimidazo[1,5-a]pyridine and (b) (+)-5-(p-cyanophenyl)-5,6,7,8-tetrahydroimidazo[1,5-a]pyridine, especially the (−) antipode (a), or of a pharmaceutically acceptable acid addition salt thereof for contraception in female primates of reproductive age without substantially affecting the menstrual cycle of the female primate, and to a method for such contraception in female primates using such compounds, and to the use of those compounds for the preparation of compositions for such contraception in female primates.

The invention relates further to the use of

-4-[α-(4-cyanophenyl)-5-isothiazolylmethyl]-benzonitrile,

-4-[α-(4-cyanophenyl)-α-fluoro-1-(1,2,4-triazolyl)methyl]-benzonitrile,

-4-[a-(4-cyanophenyl-1-(1,2,4-triazolyl)methyl]-benzonitrile,

-4-[α-(4-cyanophenyl)-(2-tetrazolyl)methyl]-benzonitrile,

-4-[α-(4-cyanophenyl)-1-(1,2,3-triazolyl)methyl]-benzonitrile,

-4-[α-(4-cyanophenyl)-1-imidazolylmethyl]-benzonitrile, or of a pharmaceutically acceptable salt thereof for contraception in female primates of reproductive age in a dose at which the menstrual cycle of the female primate remains substantially unaffected, and to a method for such contraception in female primates using such compounds, and to the use of those compounds for the preparation of compositions for such contraception in female primates.

As explained hereinbefore, aromatase inhibitors can be used to prepare pharmaceutical compositions for the inhibition of fertilisation or implantation in female primates without the female cycle being substantially affected thereby.

The pharmaceutical compositions that can be prepared according to the invention are compositions for enteral, such as peroral or rectal, administration, also for transdermal or sublingual administration, and for parenteral, for example intravenous, subcutaneous and intramuscular, administration. Suitable unit dose forms, especially for peroral and/or sublingual administration, for example dragées, tablets or capsules, comprise preferably from approximately 0.01 mg to approximately 20 mg, especially from approximately 0.1 mg to approximately 10 mg, of one of the above-mentioned compounds or of a pharmaceutically acceptable salt thereof, together with pharmaceutically acceptable carriers. The proportion of active ingredient in such pharmaceutical compositions is from approximately 0.001% to approximately 60%, preferably from approximately 0.1% to approximately 20%.

Suitable excipients for pharmaceutical compositions for oral administration are especially fillers, such as sugars, for example lactose, saccharose, mannitol or sorbitol, cellulose preparations and/or calcium phosphates, for example tricalcium phosphate or calcium hydrogen phosphate, and binders, such as starches, for example corn, wheat, rice or potato starch, gelatin, tragacanth, methylcellulose and/or hydroxypropylcellulose, disintegrators, such as the above-mentioned starches, also carboxymethyl starch, cross-linked polyvinylpyrrolidone, agar, alginic acid or a salt thereof, such as sodium alginate, and/or cellulose, for example in the form of crystals, especially in the form of microcrystals, and/or flow regulators and lubricants, for example silicic acid, talc, stearic acid or salts thereof, such as magnesium or calcium stearate, cellulose and/or polyethylene glycol.

Dragée cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable solvents or solvent mixtures, or, for the preparation of enteric coatings, solutions of suitable cellulose preparations, such as acetylcellulose phthalate or hydroxypropylmethylcellulose phthalate.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable oily excipients, such as fatty oils, paraffin oil or liquid polyethylene glycols, to which stabilisers and/or anti-bacterial agents may also be added. There may also be used capsules that are easily bitten through, in order to achieve by means of the sublingual ingestion of the active ingredient that takes place as rapid an action as possible.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. There may also be used gelatin rectal capsules, which contain a combination of the active ingredient with a base material. Suitable base materials are, for example, liquid triglycerides, polyethylene glycols or paraffin hydrocarbons.

Suitable formulations for transdermal administration comprise the active ingredient together with a carrier. Advantageous carriers include absorbable pharmacologically acceptable solvents that serve to facilitate the passage through the skin of the host. Transdermal systems are usually in the form of a bandage that comprises a support, a supply container containing the active ingredient, if necessary together with carriers, optionally a separating device that releases the active ingredient onto the skin of the host at a controlled and established rate over a relatively long period of time, and means for securing the system to the skin.

Suitable for parenteral administration are especially aqueous solutions of an active ingredient in water-soluble form, for example in the form of a water-soluble salt, and also suspensions of active ingredient, such as corresponding oily injection suspensions, there being used suitable lipophilic solvents or vehicles, such as fatty oils, for example sesame oil, or synthetic fatty acid esters, for example ethyl oleate, or triglycerides, or aqueous injection suspensions that comprise viscosity-increasing substances, for example sodium carboxymethylcellulose, sorbitol and/or dextran, and, optionally, stabilisers.

Dyes or pigments may be added to the pharmaceutical compositions, especially to the tablets or dragée coatings, for example for identification purposes or to indicate different doses of active ingredient.

The pharmaceutical compositions of the present invention can be prepared in a manner known per se, for example by means of conventional mixing, granulating, confectioning, dissolving or lyophilising processes. For example, pharmaceutical compositions for oral administration can be obtained by combining the active ingredient with solid carriers, optionally granulating a resulting mixture, and processing the mixture or granules, if desired or necessary after the addition of suitable excipients, to form tablets or dragée cores.

The invention that is claimed is described in detail in the following Examples which are intended merely to illustrate the invention and in no way represent a limitation thereof.

Temperatures are in degrees Celsius. The following abbreviations are used: ether=diethyl ether; ethyl acetate= acetic acid ethyl ester; THF=tetrahydrofuran; hexane=n-hexane; DMSO=dimethylsulfoxide; DMF=dimethylformamide; N-fluoro-dimethylsaccharinsultam=N-fluoro-3,3-dimethyl-2,3-dihydro-1,2-benzothiazole-1,1-dioxide; TLC= thin-layer chromatography; RT=room temperature; MS(FAB)=mass spectrum ("Fast Atom Bombardment").

EXAMPLE 1

4-[α-(4-cyanophenyl)-α-fluoro-1-(1,2,4-triazolyl) methyl]-benzonitrile

A solution of 0.8 mmol of potassium hexamethyldisilazane in 1.6 ml of toluene is diluted with 5 ml of THF and, after cooling to −78°, a solution of 190 mg of 4-[α-(4-cyanophenyl)-1-(1,2,4-triazolyl)methyl]-benzonitrile (see EP-A-236 940, Ex. 20a) in 3 ml of THF is added thereto. After stirring for 1 hour at the same temperature, there are added dropwise to the dark-red solution 301 mg of N-fluoro-dimethylsaccharinsultam in 3 ml of THF. After a further 1.5 hours at −78°, the reaction mixture is heated to RT in the course of 1 hour and poured onto a saturated solution of ammonium chloride in water and then extracted with methylene chloride. Drying over magnesium chloride and concentration of the solution by evaporation yield the crude product, which is purified by flash chromatography (SiO$_2$, hexane/ethyl acetate 9:1, 4:1 to 1:1). TLC (SiO$_2$, CHCl$_3$/ methanol 9:1, Rf=0.85); IR (KBr): 2220 cm$^{-1}$; $^1$H-NMR (CDCl$_3$): δ(ppm)=7.46 and 7.76 (8H,m), 8.07 (1H,s), 8.16 (1H,s).

EXAMPLE 2:

4-[α-(4-cyanophenyl)-α-fluoro-(2-tetrazolyl)methyl]-benzonitrile

Analogously to Example 1,4-[α-(4-cyanophenyl)-(2-tetrazolyl)methyl]-benzonitrile (see EP-A-408 509, Ex. 7 and 2) is converted using N-fluoro-dimethylsaccharinsultam into the title compound; m.p. 145°–146°.

EXAMPLE 3

4-[α-(4-cyanophenyl)-α-fluoro-(1-tetrazolyl) methyl]-benzonitrile

Analogously to Example 1, 4-[α-(4-cyanophenyl)-(1-tetrazolyl)methyl]-benzonitrile (see EP-A-408 509, Ex. 7) is converted using N-fluoro-dimethylsaccharinsultam into the title compound.

EXAMPLE 4

4-[α-(4-cyanophenyl)-α-fluoro-(1-imidazolyl) methyl]-benzonitrile

Analogously to Example 1, 1.075 g of 4-[α-(4-cyanophenyl)-(1-imidazolyl)methyl]benzonitrile (see EP-A-236 940, Ex. 2a, 3, 4 and 23) is converted using 930 mg of potassium hexamethyldisilazane and 1.7 g of N-fluoro-dimethylsaccharinsultam into the title compound; m.p. 133°, MS(FAB): (M+H)$^+$=303, TLC (methylene chloride/methanol 9:1): Rf=0.7.

EXAMPLE 5

1-methyl-6-[α-(4-chlorophenyl)-α-fluoro-1-(1,2,4-triazolyl)-methyl]-benzotriazole Analogously to Example 1, 1-methyl-6-[α-(4-chlorophenyl)-1-(1,2,4-triazolyl)methyl]benzotriazole (see EP-A-293 978, e.g. Example 20) is convened using N-fluoro-dimethylsaccharinsultam into the title compound.

EXAMPLE 6

4-[α-(4-cyanophenyl)-α-fluoro-1-(1,2,3-triazolyl) methyl]-benzonitrile

Analogously to Example 1, 4-[α-(4-cyanophenyl)-1-(1,2, 3-triazolyl)methyl]-benzonitrile is convened using N-fluoro-dimethylsaccharinsultam into the title compound; m.p. 138°–140°.

The starting material is prepared as follows:
(a) 4-[α-(4-cyanophenyl)-1-(1,2,3-triazolyl)methyl]-benzonitrile At constant temperature (25°–26.5°), a solution of 640 mg of 4-[1-(1,2,3-triazolyl)methyl]-benzonitrile in 5 ml of DMF is added dropwise over the course of 30 minutes to a mixture of 1.07 g of potassium tert-butoxide in 5 ml of DMF. After a further 30 minutes 20°, a solution of 525 mg of 4-fluorobenzonitrile in 5 ml of DMF is added to the reaction mixture, which is then stirred for 1.5 hours at room temperature. The reaction mixture is then cooled to 0°, diluted with CH$_2$Cl$_2$ and neutralised with 6N HCl. The reaction mixture is concentrated and taken up in water/CH$_2$Cl$_2$ and the aqueous phase is separated off. The organic phase is washed with brine, dried over sodium sulfate and concentrated. The crude product is purified by column chromatography (SiO$_2$, toluene to toluene/ethyl acetate 3:1) and crystallised from CH$_2$Cl$_2$/ethanol/hexane, to yield starting material (a), m.p. >230°; IR (CH$_2$Cl$_2$): 2230, 1605, 1500, 1160 cm$^{-1}$.

The precursor for the preparation of starting material (a) is prepared as follows:
(1) 4-[1-(1,2,3-triazolyl)methyl]-benzonitrile 8 g of 1,2,3-triazole, 10.67 g of potassium carbonate and 750 mg of potassium iodide are added in succession to a solution of 15.13 g of 4-bromomethylbenzonitrile in 375 ml of acetone. The reaction mixture is then stirred for 7.5 hours at 55° and then cooled and concentrated. The residue is dissolved in CH$_2$Cl$_2$ and washed in succession with water and brine. After drying over sodium sulfate, the solution is concentrated and the resulting crude product is purified by column chromatography (SiO$_2$, toluene/ethyl acetate 3:19), yielding precursor (1), IR (CH$_2$Cl$_2$): 2230, 1615, 1225, 1075 cm$^{-1}$.

EXAMPLE 7

7-cyano-4-[α-(4-cyanophenyl)-α-fluoro-1-(1,2,4-triazolyl)methyl]-2,3-dimethylbenzo[b]furan Analogously to Example 1, 7-cyano-4-[α-(4-cyanophenyl)-1-(1,2,4-triazolyl)methyl]-2,3-dimethylbenzol[b]furan is convened using N-fluoro-dimethylsaccharinsultam into the title compound.

The starting material is prepared as follows:
(a) 7-cyano-4-[α-(4-cyanophenyl )-1-(1,2,4-triazolyl)methyl]-2,3-dimethylbenzo[b]furan Analogously to Example 6(a), 252 mg of 7-cyano-4-[1-(1,2,4-triazolyl)methyl]-2,3-dimethylbenzol[b]furan (see EP-A-445 073, Ex. 2 and 1) are converted using 308 mg of potassium tert-butoxide and 152 mg of 4-fluorobenzonitrile in DMF into starting material (a), m.p. (ether/hexane): 200°–202°; IR (CH$_2$Cl$_2$): 3051, 1613, 1499, 1351, 1104 cm$^{-1}$.

EXAMPLE 8

4-[α-(4-bromophenyl)-α-fluoro-1-(1,2,4-triazolyl)methyl]-benzonitrile

Analogously to Example 1, 4-[α-(4-bromophenyl)-1-(1,2,4-triazolyl)methyl]-benzonitrile is converted using N-fluoro-dimethylsaccharinsultam into the title compound.

The starting material is prepared as follows:
(a) 4-[α-(4-bromophenyl)-1-(1,2,4-triazolyl)methyl]-benzonitrile Analogously to Example 6(a), 190 mg of 1-(4-bromobenzyl)-1,2,4-triazole are converted using 188 mg of potassium tert-butoxide and 106 mg of 4-fluorobenzonitrile into starting material (a); $^1$H-NMR (CDCl$_3$): δ=6.73 (1H,s), 7.05 and 7.55 (4H,m), 7.2 and 7.68(4H,m), 8.02 (1H,s), 8.05 (1H,s).

The precursor for the preparation of starting material (a) is prepared as follows:
(1) 1-(4-bromobenzyl)-1,2,4-triazole A mixture of 1 g of 4-bromobenzyl bromide, 0.41 g of 1,2,4-triazole, 0.55 g of potassium carbonate and 33 mg of potassium iodide in 30 ml of acetone is stirred for 20 hours at 50°. The solid material is removed by filtration and the solution is concentrated by evaporation. The resulting crude precursor (1) is purified by column chromatography (SiO$_2$, hexane/ethyl acetate 1:1) and crystallised from ether; m.p. 77°–79°; $^1$H-NMR (CDCl$_3$): δ=5.3 (2H,s), 7.15 and 7.5 (4H,m), 7.95 (1H,s), 8.08 (1H,m).

EXAMPLE 9

4-[α-(4-cyanophenyl)-α-fluoro-(5-pyrimidyl)methyl]-benzonitrile

Analogously to Example 1, 4-[α-(4-cyanophenyl)-(5-pyrimidyl)methyl]-benzonitrile is converted using N-fluoro-dimethylsaccharinsultam into the title compound.

The starting material is prepared as follows:
(a) 4-[α-(4-cyanophenyl)-(5-pyrimidyl)methyl]-benzonitrile 1.25 g (5.53 mmol) of tin(II) chloride dihydrate and 3.2 ml of conc. HCl are added to a solution of 863 mg (2.76 mmol) of 4-[α-(4-cyanophenyl)-α-hydroxy-(5-pyrimidyl)methyl]-benzonitrile [Example 15(b2)] in 10 ml of glacial acetic acid and the reaction mixture is boiled under reflux for 2 hours. After cooling, the reaction mixture is poured onto a large amount of water. The precipitate is filtered off with suction, washed with water, dried and dissolved in 4 ml of THF. 0.23 ml of pyridine is added to that solution, which is then stirred for 3 hours at room temperature and filtered and the filtrate is concentrated by evaporation. The resulting oily residue is purified by column chromatography (100 g of silica gel/ethyl acetate ) and corresponds to the title compound, m.p. 140°–141° (from ether/petroleum ether); Rf value: 0.25 (silica gel/ethyl acetate); IR (CH$_2$Cl$_2$): 2223 cm$^{-1}$; $^1$H-NMR (CDCl$_3$): δ=5.53 (s, 1H); 7.24 (d,4H); 7.68 (d,4H); 8.48 (s, 2H); 9.18 (s, 1H).

EXAMPLE 10

4-[α-(4-bromophenyl)-α-fluoro-(5-pyrimidyl)methyl]-benzonitrile

Analogously to Example 1, 4-[α-(4-bromophenyl)-(5-pyrimidyl)methyl]-benzonitrile is converted using N-fluoro-dimethylsaccharinsultam into the title compound.

The starting material is prepared as follows:
(a) 4-[α-(4-bromophenyl)-(5-pyrimidyl)methyl]-benzonitrile Analogously to Example 9a, 4-[α-(4-bromophenyl)-α-hydroxy-(5-pyrimidyl)methyl]benzonitrile [Example 15(b 1)] is reduced in glacial acetic acid with tin(II) chloride dihydrate and conc. HCl.

EXAMPLE 11

4-[α-(4-cyanophenyl)-α-fluoro-(3-pyridyl)methyl]-benzonitrile

Analogously to Example 1, 4-[α-(4-cyanophenyl)-(3-pyridyl)methyl]-benzonitrile (see EP-A-236 940, Ex. 21) is converted using N-fluoro-dimethylsaccharinsultam into the title compound.

EXAMPLE

4-[α-(4-cyanophenyl)-α-fluoro-1-(1,2,4-triazolyl)methyl]-benzonitrile 10 ml of THF are cooled to −30°. First 0.17 ml (1.2 mmol) of diisopropylamine and then 0.75 ml (1.2 mmol) of a 1.6M solution of n-butyllithium in hexane is added and the reaction mixture is cooled to −70 °. 285 mg(1 mmol) of 4-[α-(4-cyanophenyl)-1-(1,2,4-triazolyl)methyl]-benzonitrile (see EP-A-236 940, 20a), dissolved in 4 ml of THF, are slowly added dropwise and the reaction mixture is stirred for 3 hours at −70°. Then 346.8 mg(1.2 mmol) of N-fluoro-2,4,6-trimethylpyridinium-trifluoromethylsulfonate are added, whereupon the previously dark-red solution slowly loses its colour. The reaction mixture is allowed to warm to RT and is then poured onto a saturated aqueous ammonium chloride solution and extracted with methylene chloride. The organic extracts are dried over magnesium chloride and concentrated by evaporation, yielding the crude product which is purified by flash chromatography (SiO$_2$, hexane/ethyl acetate 9:1, 4:1 to 1:1). TLC (SiO$_2$, CHCl$_3$/methanol 9:1): Rf=0.85; IR (KBr): 2220 cm$^{-1}$; $^1$H-NMR (CDCl$_3$): δ=7.46 and 7.76 (8H, m); 8.07 (1H, s), 8.16 (1H, s).

EXAMPLE 13

7-bromo-4-[α-(4-cyanophenyl)-αfluoro-(1-imidazolyl)methyl]-2,3-dimethylbenzo[b]furan

Analogously to Example 1, 7-bromo-4-[α-(4-cyanophenyl)-(1-imidazolyl)methyl]-2,3-dimethylbenzo[b]furan is converted using N-fluoro-dimethylsaccharinsultam into the title compound.

The starting material is prepared as follows:
(a) 7-bromo-4-[α-(4-cyanophenyl)-(1-imidazolyl)methyl]-2,3-dimethylbenzo[b]furan Analogously to Example 6(a), 610 mg of 7-bromo-4-(1-imidazolylmethyl)-2,3-dimethylbenzo[b]furan (see EP-A-445 073, Ex. 3) are converted using 617 mg of potassium tert-butoxide and 303 mg of 4-fluorobenzonitrile in DMF into starting material (a) and crystallised from ether; m.p. 220°–223°; IR (CH$_2$Cl$_2$): 2231, 1674, 1629, 1490, 1199, 1109 cm$^{-1}$.

EXAMPLE 14

7-bromo-4-[α-(4-cyanophenyl)-α-fluoro-1-(1,2,4-triazolyl)methyl]-2,3-dimethylbenzo[b]furan

Analogously to Example 1, 7-bromo-4-[α-(4-cyanophenyl)-1-(1,2,4-triazolyl)methyl]-2,3-dimethylbenzo[b]furan is converted using N-fluoro-dimethylsaccharinsultam into the title compound.

The starting material is prepared as follows:
(a) 7-bromo-4-[α-(4-cyanophenyl)-1-(1,2,4-triazolyl)methyl]-2,3-dimethylbenzo[b]furan Analogously to Example 6(a), 612 mg of 7-bromo-4-[1-(1,2,4-triazolyl)methyl]2,3-dimethylbenzo[b]furan (see EP-A-445 073, Ex. 1) are converted using 617 mg of potassium tert-butoxide and 303 mg of 4-fluorobenzonitrile in DMF into starting material (a) and crystallised from ether/acetate, m.p. 198°–200°, IR (CH$_2$Cl$_2$): 2231, 1629, 1498, 1347, 1254, 1200, 1015 cm$^{-1}$.

EXAMPLE 15

4-[α-(4-cyanophenyl)-α-fluoro-(5-pyrimidyl)methyl]-benzonitrile

0.35 g (2.0 mmol) of piperidino-sulfur trifluoride is added to a solution of 0.62 g (2.0 mmol) of 4-[α-(4-cyanophenyl)-α-hydroxy-(5-pyrimidyl)methyl]-benzonitrile in 10 ml of 1,2-dichloroethane and the reaction mixture is stirred for 48 hours at 50° and then washed with water, with a saturated sodium hydrogen carbonate solution and again with water, dried over magnesium sulfate and concentrated by evaporation. The oily residue is purified by column chromatography (100 g of silica gel/ethyl acetate) and corresponds to the title compound, IR (CH$_2$C$_2$): 2220 cm$^{-1}$; $^1$H-NMR (CDCl$_3$): δ=7.20 (d,4H), 7.66 (d,4H), 8.43 (s,2H), 9.15 (s, 1H).

The starting material is prepared as follows:
(a) α,α-bis(4-bromophenyl)-5-pyrimidinemethanol With stirring and with the exclusion of moisture, a solution of 20 ml of 1.6N n-butyllithium in hexane is added dropwise in the course of 30 minutes to a solution, cooled to −75°, of 5.2 g (33 mmol) of 5-bromopyrimidine and 10.7 g (31.2 mmol) of 4,4'-dibromobenzophenone in 130 ml of THF. The reaction mixture is stirred for a further 0.5 hours at −75° and then for 16 hours at room temperature; then, while cooling with ice, it is hydrolysed by the addition of 20 ml of water. The organic phase is separated off and diluted with ethyl acetate. The solution is washed with 2N HCl and a semi-saturated sodium chloride solution, dried over sodium sulfate, filtered and concentrated by evaporation. The residue is purified by column chromatography (400 g of silica gel, methylene chloride/ethyl acetate 85:15) and recrystallised from ethyl acetate, m.p. 89°–90°, R$_f$ value= 0.11 (silica gel, methylene chloride/ethyl acetate 85:15).

(b1) 4-[α-(4-bromophenyl)-α-hydroxy-(5-pyrimidyl)methyl]-benzonitrile and
(b2) 4-[α-(4-cyanophenyl)-α-hydroxy-(5-pyrimidyl)methyl]-benzonitrile A mixture of 3.7 g (8.8 mmol) of α,α-bis(4-bromophenyl)-5-pyrimidinemethanol and 2.4 g (26.4 mmol) of copper(I) cyanide in 8 ml of DMF is stirred under argon for 4 hours at 160°. The reaction mixture is then cooled to 70°, a solution of 6.4 g (39.6 mmol) of iron(III) chloride in 20 ml of 2N HCl is added dropwise thereto and the reaction mixture is stirred thoroughly for 20 minutes at that temperature. After cooling, the reaction mixture is extracted with ethyl acetate. The organic phase is washed with a semi-saturated sodium chloride solution, dried over sodiumsulfate and concentrated by evaporation. The residue is purified by column chromatography (200 g of silica gel, hexane/ethyl acetate 1:2) and separated into compounds (b1) and (b2), yielding 4-[α-(4-bromophenyl)-α-hydroxy(5-pyrimidyl)methyl]-benzonitrile in the form of a pale yellow amorphous product, IR (CH$_2$Cl$_2$): 2190, 3530 cm$^{-1}$, R$_f$ value=0.27 (silica gel, hexane/ethyl acetate 1:2), and 4-[α-(4-cyanophenyl)-α-hydroxy-(5-pyrimidyl)methyl]-benzonitrile, m.p. 228°–230°(from ethyl acetate), IR (Nujol): 2225, 3150 (broad) cm$^{-1}$, R$_f$ value: 0.14; $^1$H-NMR (DMSO-d$_6$): δ=7.42 (s, 1H); 7.55 (d, 4H); 7.86 (d, 4H); 8.67 (s, 2H); 9.16 (s, 1H).

EXAMPLE 16

4-[α-(4-bromophenyl)-α-fluoro-(5-pyrimidyl)methyl]-benzonitrile

Analogously to Example 15, 4-[α-(4-bromophenyl)-α-hydroxy-(5-pyrimidyl)methyl]benzonitrile [Example 15(b1)] in 1,2-dichloroethane is reacted with piperidinosulfur trifluoride.

EXAMPLE 17

4-[α-(4-cyanophenyl)-α-fluoro-(2-tetrazolyl)methyl]-benzonitrile

At −5°, 399 mg of potassium hexamethyldisilazane are dissolved in 4 ml of abs. toluene and diluted with 12 ml of abs. THF. The solution is cooled to −75° and in the course of 10 minutes a solution of 475 mg of 4-[α-(4-cyanophenyl)-(2-tetrazolyl)methyl]-benzonitrile (see EP-A-408 509, Ex. 7 and 2) in 7.5 ml of abs. THF is added dropwise thereto. The dark-red reaction mixture is stirred for a further 1 hour at the same temperature and then in the course of 15 minutes a solution of 0.75 g of N-fluoro-dimethylsaccharinsultam in 7.5 ml of abs. THF is added thereto; stirring is continued for 1.5 hours and then the reaction mixture is heated to RT in the course of 1 hour. The solution is poured onto 50 ml of a saturated aqueous sodium chloride solution and extracted with methylene chloride. The organic phase is washed with brine and, after drying, concentrated over sodium sulfate. The resulting crude product is stirred three times with ether, purified by column chromatography (silica gel, ethyl acetate/hexane 1:1) and crystallised from hexane; m.p.

145°–146°, MS(FAB): (M+H)$^+$=305, TLC (ethyl acetate/hexane 1:1): Rf=0.5.

EXAMPLE 18

4-[α-(4-cyanophenyl)-α-fluoro-1-(1,2,3-triazolyl)methyl]-benzonitrile

A solution, cooled to –5°, of 798 mg of potassium hexamethyldisilazane in 8 ml of abs. toluene is diluted with 25 ml of abs. THF, cooled to –75° and, in the course of 15 minutes, a solution of 950 mg of 4-[α-(4-cyanophenyl)-1-(1,2,3-triazolyl)methyl]-benzonitrile (Ex. 6a) in 15 ml of abs. THF and 1 ml of abs. DMF is added thereto. After stirring for 1 hour at –75°, a solution of 1.5 g of N-fluorodimethylsaccharinsultam in 15 ml of THF is added. After stirring for a further 1.5 hours, the cooling bath is removed and the reaction mixture warms to RT in the course of 1 hour. The reaction mixture is poured onto 100 ml of a saturated aqueous ammonium chloride solution and extracted with methylene chloride. The organic phase is washed with brine, dried over sodium sulfate and concentrated. The resulting crude product is stirred twice with ether and purified by column chromatography (silica gel, ethyl acetate/hexane 1:1); m.p. 138–140°, MS(FAB): (M+H)$^+$= 304, TLC (ethyl acetate/hexane 1:1): Rf =0.41.

EXAMPLE 19

Contraceptive action of Fadrozol hydrochloride without substantial effect on the menstrual cycle A group of five female bonnet-monkeys (*M. Radiata*) are cohabited in the fertile phase of the cycle (day 9–13; preovulatory and ovulatory phase) with male members of the same species that have proved to be fertile. After 4 days (day 13 of the cycle), the males are removed. On the evening of the 13th day of the cycle, the female animals are fitted with mini Alzet pumps that release 500 µg of Fadrozol hydrochloride (5-(p-cyanophenyl)5,6,7,8-tetrahydroimidazo[1,5-a]pyridine hydrochloride) per day continuously. Towards the end of the cycle (day 26), the Alzet pumps are removed. This procedure is repeated during the next three cycles. Under the same experimental conditions, a control group, likewise of five bonnet-monkeys, that is not treated with Fadrozol hydrochloride is conducted. In order to assess the regularity of the cycles, the serum oestradiol and progesterone levels are measured throughout the experiment. In addition, the onset of menstruation at the expected time is monitored.

Under these experimental conditions, 80% of the untreated control animals become pregnant, whereas in the case of the animals treated with Fadrozol hydrochloride, pregnancy does not occur in a single case over three treated cycles. All the animals treated with Fadrozol hydrochloride have normal cycles; this is monitored using the serum hormone values and the occurrence of menstruation at the expected time. Treatment with Fadrozol hydrochloride has substantially no effect on the cycle and the length of the luteal phase, the progesterone profile and follicle function in the subsequent cycle. The contraceptive action of Fadrozol hydrochloride is reversible, since only a short time after cohabitation the animals originally treated become pregnant.

EXAMPLE 20

100 00 100 mg tablets, each comprising 0.2 mg of active ingredient, are prepared:

| Composition: | |
|---|---|
| 5-(p-cyanophenyl)-5,6,7,8-tetrahydroimidazo[1,5-a]pyridine hydrochloride | 2.00 g |
| silica, colloidal | 2.00 g |
| cellulose, microcrystalline | 100.00 g |
| lactose, spray-dried | 836.00 g |
| magnesium stearate | 10.00 g |
| sodium carboxymethylcellulose | 50.00 g |
| | 1000.00 g |

All the constituents of the tablet core are mixed together. As soon as a homogeneous mixture is obtained, it is compressed to form tablet cores.

EXAMPLE 21

10 000 100 mg tablets, each comprising 1 mg of active ingredient, are prepared:

| Composition: | |
|---|---|
| (-)-5-(p-cyanophenyl)-5,6,7,8-tetrahydroimidazo[1,5-a]pyridine hydrochloride | 10.00 g |
| lactose, crystalline | 740.00 g |
| cellulose, microcrystalline | 230.00 g |
| silica, colloidal | 10.00 g |
| magnesium stearate | 10.00 g |
| | 1000.00 g |

All the constituents of the tablet core are mixed together. As soon as a homogeneous mixture is obtained, it is compressed to form tablet cores.

I claim:

1. A method for the contraception in a female primate of reproductive age comprising administering to the female primate an aromatase inhibitor in a dose at which the menstrual cycle of the female primate remains substantially unaffected.

2. A method according to claim 1, wherein the primates are humans.

3. A method according to claim 1, wherein the aromatase inhibitor exhibits an IC$_{50}$ value of 10$^{-5}$M or lower for in vitro inhibition of aromatase activity.

4. A method according to claim 1, wherein the aromatase inhibitor exhibits an IC$_{50}$ value of 10$^{-7}$M or lower for in vitro inhibition of aromatase activity.

5. A method according to claim 1, wherein in the case of in vivo aromatase inhibition the aromatase inhibitor is effective at a dose of 10 mg/kg or less.

6. A method according to claim 1, wherein in the case of in vivo aromatase inhibition the aromatase inhibitor is effective at a dose of 0.1 mg/kg or less.

7. A method according to claim 1, wherein 5-(p-cyanophenyl)-5,6,7,8tetrahydroimidazo[1,5-a]pyridine, or a pharmaceutically acceptable acid addition salt thereof, is the aromatase inhibitor.

8. A method according to claim 1, wherein (-)-5-(p-cyanophenyl)-5,6,7,8-tetrahydroimidazo[1,5-a]pyridine, or a pharmaceutically acceptable acid addition salt thereof, is the aromatase inhibitor.

9. A method according to claim 1, wherein the aromatase inhibitor is a compound selected from the group consisting of -4-[α-(4-cyanophenyl)-5-isothiazolylmethyl]-benzonitrile, -4-[α-(4-cyanophenyl)-α-fluoro-1-(1,2,4-triazolyl)methyl]-benzonitrile, -4-[α-(4-cyanophenyl-1-(1,2,4-triazolyl)methyl]-benzonitrile, -4-[α-(4-cyanophenyl)-(2-tetrazolyl)methyl]-benzonitrile, -4-[α-(4-cyanophenyl)-1-(1,2,3-triazolyl)methyl]-benzonitrile, -4-[α-(4-cyanophenyl)-1-imidazolylmethyl]-benzonitrile, and a pharmaceutically acceptable salt thereof.

10. A method according to claim 1, wherein the aromatase inhibitor is selected from the group consisting of a compound of formula (I)

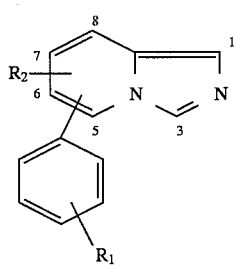

wherein $R_1$ is hydrogen, lower alkyl; lower alkyl substituted by hydroxy, lower alkoxy, lower alkanoyloxy, lower alkanoyl, amino, lower alkylamino, di-lower alkylamino, halogen, sulfo, carboxy, lower alkoxycarbonyl, carbamoyl or by cyano; nitro, halogen, hydroxy, lower alkoxy, lower alkanoyloxy, phenylsulfonyloxy, lower alkylsulfonyloxy, mercapto, lower alkylthio, lower alkylsulfinyl, lower alkylsulfonyl, lower alkanoylthio, amino, lower alkylamino, di-lower alkylamino, lower alkyleneamino, N-morpholino, N-thiomorpholino, N-piperazino that is unsubstituted or lower alkyl-substituted in the 4-position, tri-lower alkylammonio, sulfo, lower alkoxysulfonyl, sulfamoyl, lower alkylsulfamoyl, di-lower alkylsulfamoyl, formyl; iminomethyl that is unsubstituted or substituted at the nitrogen atom by hydroxy, lower alkoxy, lower alkanoyloxy, lower alkyl, phenyl or by amino; $C_2$–$C_7$alkanoyl, benzoyl, carboxy, lower alkoxycarbonyl, carbamoyl, lower alkylcarbamoyl, di-lower alkylcarbamoyl, cyano, 5-tetrazolyl, unsubstituted or lower alkyl-substituted 4,5-dihydro-2-oxazolyl or hydroxycarbamoyl; and $R_2$ is hydrogen, lower alkyl, phenyl-lower alkyl, carboxy-lower alkyl, lower alkoxycarbonyl-lower alkyl, halogen, hydroxy, lower alkoxy, lower alkanoyloxy, mercapto, lower alkylthio, phenyl-lower alkylthio, phenylthio, lower alkanoylthio, carboxy, lower alkoxycarbonyl or lower alkanoyl;

a 7,8-dihydro derivative thereof;

a compound of formula (I*)

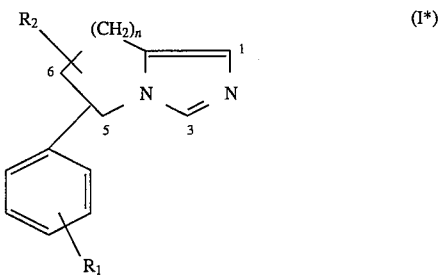

wherein n is 0, 1, 2, 3 or 4; and $R_1$ and $R_2$ are as defined above; the phenyl ring in the radicals phenylsulfonyloxy, phenyliminomethyl, benzoyl, phenyl-lower alkyl, phenyl-lower alkylthio and phenylthio may be unsubstituted or substituted by lower alkyl, lower alkoxy or by halogen; and the two substituents $C_6H_4$-$R_1$ and $R_2$ may be linked to each of the saturated carbon atoms of the saturated ring, either both to the same carbon atom or both to different carbon atoms; and a pharmaceutically acceptable salt thereof.

11. A method according to claim 10, wherein the aromatase inhibitor is selected from the group consisting of 5-(p-cyanophenyl)imidazo[1,5-a]pyridine, 5-(p-ethoxycarbonylphenyl)imidazo[1,5-a]pyridine, 5-(p-carboxyphenyl)imidazo[1,5-a]pyridine, 5
-(p-tert-butylaminocarbonylphenyl)imidazo[1,5-a]pyridine, 5-(p-ethoxycarbonylphenyl)-5,6,7,8-tetrahydroimidazo[1,5-a]pyridine, 5-(p-carboxyphenyl)-5,6,7,8-tetrahydroimidazo[1,5-a]pyridine, 5-(p-carbamoylphenyl)-5,6,7,8-tetrahydroimidazo[1,5-a ]pyridine, 5-(p-tolyl)-5,6,7,8-tetrahydroimidazo[1,5-a ]pyridine, 5-(p-hydroxymethylphenyl)imidazo[1,5;a]pyridine, 5-(p-cyanophenyl)-7,8-dihydroimidazo[1,5-a]pyridine, 5-(p-bromophenyl)-5,6,7,8-tetrahydroimidazo[1,5-a]pyridine, 5-(p-hydroxymethylphenyl)-5,6,7,8-tetrahydroimidazo[1,5-a]pyridine, 5-(p-formylphenyl)-5,6,7,8-tetrahydroimidazo[1,5-a]pyridine, 5-(p-cyanophenyl)-5-methylthio-5,6,7,8-tetrahydroimidazo[1,5-a]pyridine, 5-(p-cyanophenyl)-5-ethoxycarbonyl-5,6,7,8-tetrahydroimidazo[1,5-a]pyridine, 5-(p-aminophenyl)-5,6,7,8-tetrahydroimidazo[1,5-a]pyridine, 5-(p-formylphenyl)imidazo[1,5-a]pyridine, 5-(p-carbamoylphenyl)imidazo[1,5-a]pyridine, 5H-5-(4-tert-butylaminocarbonylphenyl)-6,7-dihydropyrrolo[1,2-c]imidazole, 5H-5-(4-cyanophenyl)-6,7-dihydropyrrolo[1,2-c]imidazole, 5H-5-(4-cyanophenyl)-6,7,8,9-tetrahydroimidazo[1,5-a]azepine, 5-(4-cyanophenyl)-6-ethoxycarbonylmethyl-5,6,7,8-tetrahydroimidazo[1,5-a]pyridine, 5-(4-cyanophenyl)-6-carboxymethyl-5,6,7,8-tetrahydroimidazo[1,5-a ]pyridine, 5-benzyl-5-(4-cyanophenyl)-5,6,7,8-tetrahydroimidazo[1,5-a]pyridine, 7-(p-cyanophenyl)-5,6,7,8-tetrahydroimidazo[1,5-a]pyridine, 7-(p-carbamoylphenyl)-5,6,7,8-tetrahydroimidazo[1,5-a]pyridine, and 5-(p-cyanophenyl)-5,6,7, 8-tetrahydroimidazo[1,5-a ]pyridine.

12. A method according to claim 10, wherein the compound of formula (b) is selected from the group consisting of 4-[alpha-(4-cyanophenyl)-1-imidazolylmethyl]-benzonitrile, 4-[alpha-(3-pyridyl)-1-imidazolylmethyl]-benzonitrile, 4-[alpha-(4-cyanobenzyl)-1-imidazolylmethyl]-benzonitrile, 1-(4-cyanophenyl)-1-(1-imidazolyl)-ethylene, 4-[alpha-(4-cyanophenyl)-1-(1,2,4-triazolyl)methyl]-benzonitrile, and 4-[alpha-(4-cyanophenyl)-3-pyridylmethyl]-benzonitrile.

13. A method according to claim 1, wherein the aromatase inhibitor is a compound of formula (b)

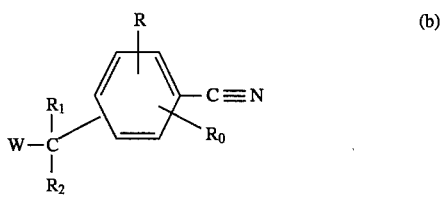

(b)

wherein

R and $R_0$, independently of one another, are each hydrogen or lower alkyl, or R and $R_0$ at adjacent carbon atoms, together with the benzene ring to which they are bonded, form a naphthalene or tetrahydronaphthalene ring;

$R_1$ is hydrogen, lower alkyl, aryl, aryl-lower alkyl or lower alkenyl;

$R_2$ is hydrogen, lower alkyl, aryl, aryl-lower alkyl, (lower alkyl, aryl or aryl-lower alkyl)-thio or lower alkenyl; or $R_1$ and $R_2$ together are lower alkylidene or $C_4$–$C_6$alkylene;

W is 1-imidazolyl, 1-(1,2,4 or 1,3,4)-triazolyl, 3-pyridyl, each of which may be substituted by lower alkyl; and aryl is phenyl which may be substituted by one or two substituents from the group consisting of lower alkyl, lower alkoxy, hydroxy, lower alkanoyloxy, nitro, amino, halogen, trifluoromethyl, cyano, carboxy, lower alkoxycarbonyl, carbamoyl, N-lower alkylcarbamoyl, N,N-di-lower alkylcarbamoyl, lower alkanoyl, benzoyl, lower alkylsulfonyl, sulfamoyl, N-lower alkylsulfamoyl and N,N-di-lower alkylsulfamoyl; thienyl, indolyl, pyridyl or furyl, either unsubstituted or monosubstituted by lower alkyl, lower alkoxy, cyano or halogen;

or a pharmaceutically acceptable salt thereof.

14. A method according to claim 1, wherein the aromatase inhibitor is selected from the group consisting of a compound-of formula (c)

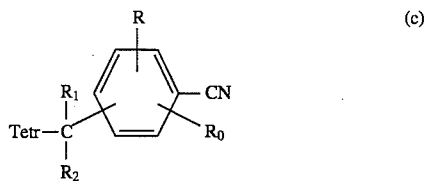

(c)

wherein

Tetr is 1- or 2-tetrazolyl that is unsubstituted or substituted in the 5-position by lower alkyl, phenyl-lower alkyl or by lower alkanoyl;

$R_1$ and R2, independently of one another, are each hydrogen; lower alkyl that is unsubstituted or substituted by hydroxy, lower alkoxy, halogen, carboxy, lower alkoxycarbonyl, (amino, lower alkylamino or di-lower alkylamino)-carbonyl or by cyano; lower alkenyl, aryl, heteroaryl, aryl-lower alkyl, $C_3$–$C_6$cycloalkyl, $C_3$–$C_6$cycloalkyl-lower alkyl, lower alkylthio, arylthio or aryl-lower alkylthio; or $R_1$ and $R_2$ together are straight-chained $C_4$–$C_6$alkylene that is unsubstituted or substituted by lower alkyl, or are a group —$(CH_2)_m$—1,2-phenylene-$(CH_2)_n$— wherein m and n, independently of one another, are each 1 or 2 and 1,2-phenylene is unsubstituted or substituted in the same way as phenyl in the definition of aryl below, or are lower alkylidene that is unsubstituted or mono- or di-substituted by aryl; and R and $R_0$, independently of one another, are each hydrogen or lower alkyl; or R and $R_0$ together, located at adjacent carbon atoms of the benzene ring, are a benzo group that is unsubstituted or substituted in the same way as phenyl in the definition of aryl below;

aryl is phenyl that is unsubstituted or substituted by one or more substituents from the group consisting of lower alkyl, lower alkoxy, hydroxy, lower alkanoyloxy, nitro, amino, halogen, trifluoromethyl, carboxy, lower alkoxycarbonyl, (amino, lower alkylamino or di-lower alkylamino)-carbonyl, cyano, lower alkanoyl, benzoyl, lower alkylsulfonyl and (amino, lower alkylamino or di-lower alkylamino)-sulfonyl; and heteroaryl is an aromatic heterocyclic radical selected from the group consisting of pyrrolyl, pyrazolyl, imidazolyl, triazolyl, tetrazolyl, furanyl, thienyl, isoxazolyl, oxazolyl, oxadiazolyl, isothiazolyl, thiazolyl, thiadiazolyl, pyridyl, pyridazinyl, pyrimidyl, pyrazinyl, triazinyl, indolyl, isoindolyl, benzimidazolyl, benzotriazolyl, benzofuranyl, benzothienyl, benzoxazolyl, benzothiazolyl, benzoxadiazolyl, benzothiadiazolyl, quinolyl and isoquinolyl that is unsubstituted or substituted in the same way as phenyl in the definition of aryl above;

a compound of formula (d)

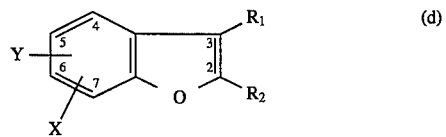

(d)

wherein

X is halogen, cyano, carbamoyl, N-lower alkylcarbamoyl, N-cycloalkyl-lower alkylcarbamoyl, N,N-di-lower alkylcarbamoyl, N-arylcarbamoyl, hydroxy, lower alkoxy, aryl-lower alkoxy or aryloxy, wherein aryl is phenyl or naphthyl, each of which is unsubstituted or substituted by lower alkyl, hydroxy, lower alkoxy, halogen or trifluoromethyl;

Y is —$CH_2$—A or hydrogen;

A is 1-imidazolyl, 1-(1,2,4-triazolyl), 1-(1,3,4-triazolyl), 1-(1,2,3-triazolyl), 1-(1,2,5-triazolyl), 1-tetrazolyl or 2-tetrazolyl; and $R_1$ and $R_2$, independently of one another, are hydrogen, lower alkyl or—$CH_2$—A, or $R_1$ and $R_2$ together are —$(CH_2)_n$—wherein n is 3, 4 or 5;

with the provisos that one of the radicals Y, $R_1$ and $R_2$ is —$CH_2$—A; when X is bromine, cyano or carbamoyl, $R_1$ and $R_2$ are not —$CH_2$—A where A is 1-imidazolyl; and when X is halogen or lower alkoxy, $R_1$ is hydrogen, and $R_2$ is hydrogen or lower alkyl, Y is —$CH_2$—A where A is other than 1-imidazolyl;

a compound of formula (e)

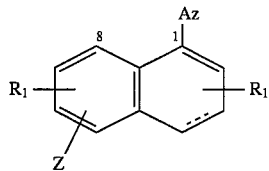
(e)

wherein the dotted line denotes an additional bond or no additional bond;

Az is imidazolyl, triazolyl or tetrazolyl bonded via a ring nitrogen atom, each of those radicals being unsubstituted or substituted at carbon atoms by lower alkyl or by aryl-lower alkyl;

Z is carboxy, lower alkoxycarbonyl, carbamoyl, N-lower alkylcarbamoyl, N,N-di-lower alkylcarbamoyl, N-arylcarbamoyl, cyano, halogen, hydroxy, lower alkoxy, aryl-lower alkoxy, aryloxy, lower alkyl, trifluoromethyl or aryl-lower alkyl; and $R_1$ and $R_2$, independently of one another, are each hydrogen, lower alkyl, lower alkoxy, hydroxy, halogen or trifluoromethyl; aryl being phenyl or naphthyl each of which is unsubstituted or substituted by one or two substituents from the group consisting of lower alkyl, lower alkoxy, hydroxy, halogen and trifluoromethyl;

with the proviso that neither Z nor $R_2$ is hydroxy in the 8-position;

a compound of formula (f)

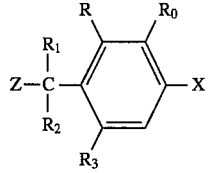
(f)

wherein

Z is a five-membered nitrogen-containing heteroaromatic ring selected from the group consisting of 5-isothiazolyl, 5-thiazolyl, 5-isoxazolyl, 5-oxazolyl, 5-(1,2,3-thiadiazolyl), 5(1,2,3-oxadiazolyl), 3-(1,2,5-thiadiazolyl), 3-(1,2,5-oxadiazolyl), 4-isothiazolyl, 4isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl);

R and $R_0$ are hydrogen or R and $R_0$ together are a benzo group that is unsubstituted or substituted by lower alkyl, lower alkoxy, hydroxy, halogen or by trifluoromethyl;

$R_1$ is hydrogen, hydroxy, chlorine or fluorine;

$R_3$ is hydrogen;

$R_2$ is hydrogen, lower alkyl or phenyl that is unsubstituted or substituted by lower alkyl, lower alkoxy, hydroxy, halogen, trifluoromethyl or by cyano; or $R_1$ and $R_2$ together are methylidene; or $R_2$ and $R_3$ together are —$(CH_2)_3$—; or $R_1$ and $R_2$ and $R_3$ together are a group =CH—$(CH_2)_2$— wherein the single bond is linked to the benzene ring; and X is cyano or X may be halogen when $R_2$ and $R_3$ together are —$(CH_2)_3$— or $R_1$ and $R_2$ and $R_3$ together are a group =CH—$(CH_2)_2$—; and pharmaceutically acceptable salts of compounds of formulae (c)–(f).

15. A method according to claim 1, wherein the aromatase inhibitor is selected from the group consisting of a compound of formula (g)

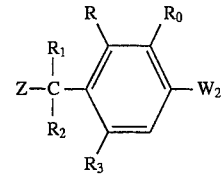
(g)

wherein

Z is a five-membered nitrogen-containing heteroaromatic ring selected from the group consisting of 5-isothiazolyl, 5-thiazolyl, 5-isoxazolyl, 5-oxazolyl, 5-(1,2,3-thiadiazolyl), 5(1,2,3-oxadiazolyl), 3-(1,2,5-thiadiazolyl), 3-(1,2,5-oxadiazolyl), 4-isothiazolyl, 4-isoxazolyl, 4-(1,2,3-thiadiazolyl), 4-(1,2,3-oxadiazolyl), 2-(1,3,4-thiadiazolyl), 2-(1,3,4-oxadiazolyl), 5-(1,2,4-thiadiazolyl) and 5-(1,2,4-oxadiazolyl);

R and $R_0$ are each hydrogen, or R and $R_0$ together are a benzo group that is unsubstituted or substituted by lower alkyl, lower alkoxy, hydroxy, halogen or by trifluoromethyl;

$R_1$ is hydrogen, hydroxy, chlorine or fluorine;

$R_3$ is hydrogen;

$R_2$ is hydrogen, lower alkyl or phenyl that is unsubstituted or substituted by lower alkyl, lower alkoxy, hydroxy, halogen, trifluoromethyl, aryl-lower alkoxy or by aryloxy; or $R_1$ and $R_2$ together are methylidene; and $W_2$ is halogen, hydroxy, lower alkoxy, aryl-lower alkoxy or aryloxy;

aryl in each case being phenyl that is unsubstituted or substituted by lower alkyl, lower alkoxy, hydroxy, halogen or by trifluoromethyl;

a compound of formula (h)

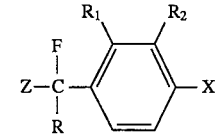
(h)

wherein

Z is imidazolyl, triazolyl, tetrazolyl, pyrrolyl, pyrazolyl, indolyl, isoindolyl, benzimidazolyl, benzopyrazolyl, benzotriazolyl, pyridyl, pyrimidyl, pyrazinyl, pyridazinyl, triazinyl, quinolinyl or isoquinolinyl, all those radicals being bonded via their heterocyclic rings and all those radicals being unsubstituted or substituted by lower alkyl, hydroxy, lower alkoxy, halogen or by trifluoromethyl;

$R_1$ and $R_2$, independently of one another, are each hydrogen or lower alkyl, or $R_1$ and $R_2$ together are $C_3$–$C_4$alkylene, or a benzo group that is unsubstituted or substituted as indicated below for aryl;

R is hydrogen, lower alkyl, aryl or heteroaryl;

X is cyano, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-aryl-lower alkylcarbamoyl, N-arylcarbamoyl, N-hydroxycarbamoyl, hydroxy, lower alkoxy, aryl-lower alkoxy or aryloxy; and X may be halogen when Z is imidazolyl, triazolyl, tetrazolyl, pyrrolyl, pyrazolyl, indolyl, isoindolyl, benzimidazolyl, benzopyrazolyl or benzotriazolyl;

R" is hydrogen, lower alkyl or lower alkanoyl;

aryl is phenyl or naphthyl, these radicals being unsubstituted or substituted by from 1 to 4 substituents selected from the group consisting of lower alkyl, lower alkenyl, lower alkynyl, lower alkylene linked to two adjacent carbon atoms, $C_3$–$C_8$cycloalkyl, phenyl-lower alkyl, phenyl; lower alkyl that is substituted in turn by hydroxy, lower alkoxy, phenyl-lower alkoxy, lower alkanoyloxy, halogen, amino, lower alkylamino, di-lower alkylamino, mercapto, lower alkylthio, lower alkylsulfinyl, lower alkylsulfonyl, carboxy, lower alkoxycarbonyl, carbamoyl, N-lower alkylcarbamoyl, N,N-di-lower alkylcarbamoyl and/or by cyano; hydroxy; lower alkoxy, halo-lower alkoxy, phenyl-lower alkoxy, phenoxy, lower alkenyloxy, halo-lower alkenyloxy, lower alkynyloxy, lower alkylenedioxy linked to two adjacent carbon atoms, lower alkanoyloxy, phenyl-lower alkanoyloxy, phenylcarbonyloxy, mercapto, lower alkylthio, phenyl-lower alkylthio, phenylthio, lower alkylsulfinyl, phenyl-lower alkylsulfinyl, phenylsulfinyl, lower alkylsulfonyl, phenyl-lower alkylsulfonyl, phenylsulfonyl, halogen, nitro, amino, lower alkylamino, $C_3$–$C_8$cycloalkylamino, phenyl-lower alkylamino, phenylamino, di-lower alkylamino, N-lower alkyl-N-phenylamino, N-lower alkyl-N-phenyl-lower alkylamino; lower alkyleneamino or lower alkyleneamino interrupted by —O—, —S— or —NR"—; lower alkanoylamino, phenyl-lower alkanoylamino, phenylcarbonylamino, lower alkanoyl, phenyl-lower alkanoyl, phenylcarbonyl, carboxy, lower alkoxycarbonyl, carbamoyl, N-lower alkylcarbamoyl, N,N-di-lower alkylcarbamoyl, N,N-lower alkylenecarbamoyl; N,N-lower alkylenecarbamoyl interrupted by —O—, —S— or —NR"—; N-cycloalkylcarbamoyl, N-(lower alkyl-substituted cycloalkyl)-carbamoyl, N-cycloalkyl-lower alkylcarbamoyl, N-(lower alkyl-substituted cycloalkyl)-lower alkylcarbamoyl, N-hydroxycarbamoyl, N-phenyl-lower alkylcarbamoyl, N-phenylcarbamoyl, cyano, sulfo, lower alkoxysulfonyl, sulfamoyl, N-lower alkylsulfamoyl, N,N-di-lower alkylsulfamoyl and N-phenylsulfamoyl; the phenyl groups occurring in the substituents of phenyl and naphthyl in turn being unsubstituted or substituted by lower alkyl, lower alkoxy, hydroxy, halogen or trifluoromethyl; and heteroaryl is indolyl, isoindolyl, benzimidazolyl, benzopyrazolyl, benzotriazolyl, benzo[b]furanyl, benzo[b]thienyl, benzoxazolyl or benzothiazolyl, those radicals being unsubstituted or substituted by from 1 to 3 identical or different substituents selected from lower alkyl, hydroxy, lower alkoxy, halogen, cyano and trifluoromethyl;

a compound of formula (i)

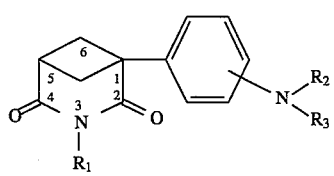

wherein $R_1$ is hydrogen; $R_2$ is hydrogen, sulfo, $C_1$–$C_7$alkanoyl or $C_1$–$C_7$alkanesulfonyl; and $R_3$ is hydrogen; or $R_1$ is $C_1$–$C_{12}$alkyl, $C_2$–$C_{12}$alkenyl, $C_2$–$C_7$alkynyl, $C_3$–$C_{10}$cycloalkyl, $C_3$–$C_{10}$cycloalkenyl, $C_3$–$C_8$cycloalkyl-$C_1$–$C_4$alkyl, $C_3$–$C_6$cycloalkyl-$C_2$–$C_4$alkenyl or $C_3$–$C_6$cycloalkenyl-$C_1$–$C_4$alkyl; $R_2$ is hydrogen, $C_1$–$C_7$alkyl, sulfo, $C_1$–$C_7$alkanoyl or $C_1$–$C_7$alkanesulfonyl; and $R_3$ is hydrogen or $C_1$–$C_7$alkyl;

a compound of formula (j)

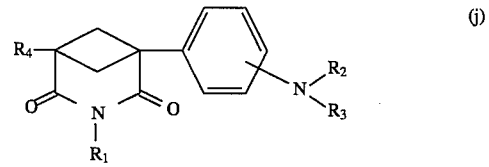

wherein $R_1$ is hydrogen, alkyl having from 1 to 12 carbon atoms, alkenyl having from 2 to 12 carbon atoms, lower alkynyl, cycloalkyl or cycloalkenyl each having from 3 to 10 carbon atoms, cycloalkyl-lower alkyl having from 4 to 10 carbon atoms, cycloalkyl-lower alkenyl having from 5 to 10 carbon atoms, cycloalkenyl-lower alkyl having from 4 to 10 carbon atoms, or aryl having from 6 to 12 carbon atoms or aryl-lower alkyl having from 7 to 15 carbon atoms, each of which is unsubstituted or substituted by lower alkyl, hydroxy, lower alkoxy, acyloxy, amino, lower alkylamino, di-lower alkylamino, acylamino or by halogen;

$R_2$ is hydrogen, lower alkyl, sulfo, lower alkanoyl or lower alkanesulfonyl;

$R_3$ is hydrogen or lower alkyl; and $R_4$ is hydrogen, lower alkyl, phenyl or phenyl substituted by -N($R_2$)($R_3$);

radicals described as "lower" containing up to and including 7 carbon atoms; and pharmaceutically acceptable salts of compounds of formulae (g)–(j).

16. A method according to claim 1, wherein the aromatase inhibitor is selected from the group consisting of a compound of formula (k)

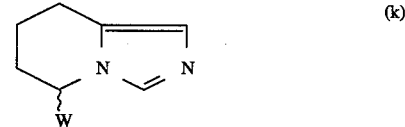

wherein

W is a 2-naphthyl or 1-anthryl radical, where each benzene ring is unsubstituted or substituted by a substituent selected from halogen, hydroxy, carboxy, cyano and nitro; or W is 4-pyridyl, 2-pyrimidyl or 2-pyrazinyl, each of those radicals being unsubstituted or substituted by a substituent selected from the group consisting of halogen, cyano, nitro, $C_1$–$C_4$alkoxy and $C_2$–$C_5$alkoxycarbonyl;

a compound of formula (l)

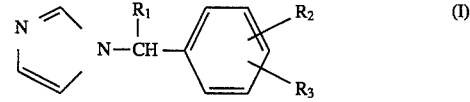

wherein $R_1$ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl;

$R_2$ is benzyloxy, 3-bromo-, 4-bromo-, 4-chloro-, 2,3-, 2,4-, 4,5- or 4,6-dichloro-benzyloxy: and R₃ is cyano; C₂–C₁₀alkanoyl that is unsubstituted or mono- or poly-substituted by halogen, methoxy, amino, hydroxy and/or by cyano; benzoyl that is unsubstituted or substituted by one or more substituents selected from the group consisting of halogen, C₁–C₄alkyl, methoxy, amino, hydroxy and cyano; carboxy, (methoxy, ethoxy or butoxy)-carbonyl, carbamoyl, N-isopropylcarbamoyl, N-phenylcarbamoyl, N-pyrrolidylcarbonyl; and a compound of formula (m)

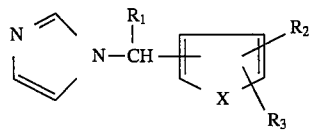

(m)

wherein

R₁ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl;

R₂ is hydrogen, halogen, cyano, methyl, hydroxymethyl, cyanomethyl, methoxymethyl, pyrrolidinylmethyl, carboxy, (methoxy, ethoxy or butoxy)-carbonyl, carbamoyl, N-isopropylcarbamoyl, N-phenylcarbamoyl, N-pyrrolidylcarbonyl; C₂–C₁₀alkanoyl that is unsubstituted or mono- or poly-substituted by halogen, methoxy, ethoxy, amino, hydroxy or cyano; or benzoyl that is unsubstituted or substituted by one or more substituents selected from the group consisting of halogen, C₁–C₄alkyl, methoxy, ethoxy, amino, hydroxy and cyano;

R₃ is hydrogen, benzyloxy, 3-bromo-, 4-bromo-, 4-chloro-, 2,3-, 2,4-, 4,5- or 4,6-dichlorobenzyloxy: and X is —CH═N—, —CH═N(—O)— or —S—;

a compound of formula (n)

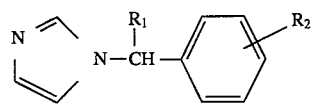

(n)

wherein

R₁ is hydrogen, methyl, ethyl, propyl, propenyl, isopropyl, butyl, hexyl, octyl, decyl, cyclopentyl, cyclohexyl, cyclopentylmethyl, cyclohexylmethyl or benzyl; and R₂ is a radical selected from the group consisting of methyl, ethyl, propyl, benzyl, phenyl and ethenyl that is substituted by hydroxy, cyano, methoxy, butoxy, phenoxy, amino, pyrrolidinyl, carboxy, lower alkoxycarbonyl or by carbamoyl; formyl or derivatised formyl that can be obtained by reaction of the formyl group with an amine or amine derivative selected from the group consisting of hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline; acetyl, propionyl, butyryl, valeryl, caproyl; benzoyl that is unsubstituted or substituted by one or more substituents selected from the group consisting of halogen, C₁–C₄alkyl, methoxy, amino, hydroxy and cyano; carboxy, (methoxy, ethoxy or butoxy)-carbonyl, carbamoyl, N-isopropylcarbamoyl, N-phenylcarbamoyl or N-pyrrolidylcarbonyl; and pharmaceutically acceptable salts of compounds of formulae (k)–(n).

17. A method according to claim 1, wherein the aromatase inhibitor is selected from the group consisting of a compound of formula (o)

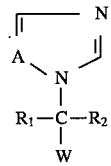

(o)

wherein

A is an N-atom or a CH radical;

W is a radical of the formula

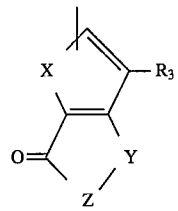

where X is an oxygen or a sulfur atom or a —CH═CH— group;

Y is a methylene group, an oxygen or a sulfur atom;

Z is a —(CH₂)n— group wherein n=1, 2 or 3;

R₁ is hydrogen, a C₁–C₁₀alkyl group or a C₃–C₇cycloalkyl group;

R₃ is hydrogen; or

R₁ together with R₃ forms a —(CH₂)ₘ— group where m=2, 3 or 4; and

R₂ is hydrogen, a C₁–C₁₀alkyl group or a C₃–C₇cycloalkyl group;

a pharmaceutically acceptable addition salt with acid of a compound of formula (o);

a compound of formula (p)

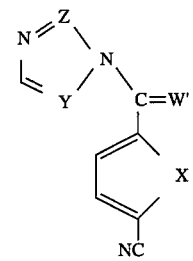

(p)

wherein

W is a cyclopentylidene, cyclohexylidene, cycloheptylidene or 2-adamantylidene radical;

X is —CH═CH—, an oxygen or a sulfur atom; and

Y and Z, independently of one another, are a methine group or a nitrogen atom;

a pharmaceutically acceptable addition salt with acid of a compound of formula (p);

a compound of formula (q)

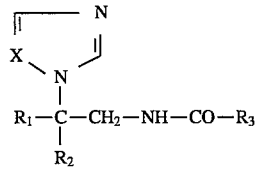

(q)

wherein

X is CH or N;

$R_1$ and $R_2$ are identical or different and are each phenyl or halophenyl; and $R_3$ is $C_1$–$C_4$alkyl; $C_1$–$C_4$alkyl substituted by CN, $C_1$–$C_4$alkoxy, benzyloxy or $C_1$–$C_4$alkoxy(mono-, di- or tri-)ethyleneoxy; $C_1$–$C_4$alkoxy, phenyl; phenyl that is substituted by halogen or cyano; a $C_5$–$C_7$cycloalkyl group that is optionally condensed by benzene, or is thienyl, pyridyl or 2- or 3-indolyl;

an acid addition salt of a compound of formula (q);

and a compound of formula (r)

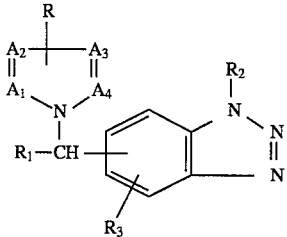

(r)

wherein

—$A_1$=$A_2$—$A_3$=$A_4$— is a divalent radical selected from the group consisting of —CH=N—CH=CH—, —CH=N—CH=N— and —CH=N—N=CH—;

R is hydrogen or $C_1$–$C_6$alkyl;

$R_1$ is hydrogen, $C_1$–$C_{10}$alkyl, $C_3$–$C_7$cycloalkyl, $Ar_1$, $Ar_2$—$C_1$—$C_6$alkyl, $C_2$–$C_6$alkenyl or $C_2$–$C_6$alkynyl;

$R_2$ is hydrogen; $C_1$–$C_{10}$alkyl that is unsubstituted or substituted by $Ar_1$; $C_3$–$C_7$cycloalkyl, hydroxy, $C_1$–$C_6$alkoxy, $Ar_1$, $C_2$–$C_6$alkenyl, $C_2$–$C_6$alkynyl, $C_3$–$C_7$cycloalkyl, bicyclo[2.2.1]-heptan-2-yl, 2,3-dihydro-1 H-indenyl, 1,2,3,4-tetrahydronaphthyl, hydroxy; $C_2$–$C_6$alkenyloxy that is unsubstituted or substituted by $Ar_2$; $C_2$–$C_6$alkynyloxy; pyrimidyloxy; di($Ar_2$)-methoxy, (1-$C_1$–$C_4$alkyl-4-piperidinyl)oxy, $C_1$–$C_{10}$alkoxy; or $C_1$–$C_{10}$alkoxy that is substituted by halogen, hydroxy, $C_1$–$C_6$alkyloxy, amino, mono- or di-($C_1$–$C_6$alkyl)amino, trifluoromethyl, carboxy, $C_1$–$C_6$alkoxycarbonyl, $Ar_1$, $Ar_2$—O—, $Ar_2$—S—, $C_3$–$C_7$cycloalkyl, 2,3-dihydro-1,4-benzodioxinyl, 1H-benzimidazolyl, $C_1$–$C_4$alkyl-substituted 1H-benzimidazolyl, (1,1'-biphenyl)-4-yl or by 2,3-dihydro-2-oxo-1H-benzimidazolyl;

$R_3$ is hydrogen, nitro, amino, mono- or di-($C_1$–$C_6$alkyl)amino, halogen, $C_1$–$C_6$alkyl, hydroxy or $C_1$–$C_6$alkoxy;

$Ar_1$ is phenyl, substituted phenyl, naphthyl, pyridyl, aminopyridyl, imidazolyl, triazolyl, thienyl, halothienyl, furanyl, $C_1$–$C_6$alkylfuranyl, halofuranyl or thiazolyl;

$Ar_2$ is phenyl, substituted phenyl or pyridyl; and

"substituted phenyl" is phenyl that is substituted by up to 3 substituents in each case selected independently of one another from the group consisting of halogen, hydroxy, hydroxymethyl, trifluoromethyl, $C_1$–$C_6$alkyl, $C_1$–$C_6$alkoxy, $C_1$–$C_6$alkoxycarbonyl, carboxy, formyl, hydroxyiminomethyl, cyano, amine, mono- and di-($C_1$–$C_6$alkyl)amino and nitro; and a pharmaceutically acceptable salt or stereochemically isomeric form of a compound of formulae (r).

18. A method according to claim 1, wherein the aromatase inhibitor is selected from the group consisting of 6-[(1H-imidazol-1-yl)-phenylmethyl]-1-methyl-1H-benzotriazole, 6-[(4-chlorophenyl)(1H-1,2,4-triazol-1-yl)methyl]-1-methyl-1H-benzotriazole, 2-(4-chlorophenyl)-1, 1-di(1,2,4-triazol-1-ylmethyl)ethanol, 2-(4-fluorophenyl)-1,1-di(1,2,4-triazol-1-ylmethyl)ethanol, 2-(2-fluoro-4-trifluoromethylphenyl)-1,1-di(1,2,4-triazol-1-ylmethyl)ethanol, 2-(2,4-dichlorophenyl)-1,1-di(1,2,4-triazol-1-ylmethyl) ethanol, 2-(4-chlorophenyl)-1,1-di(1,2,4-triazol-1-ylmethyl)-ethanol, 2-(4-fluorophenyl)-1,1-di(1,2,4-triazol-1-yl-methyl)ethanol, (1R*,2R*)-6-fluoro-2-(4-fluorophenyl)-1,2,3,4-tetrahydro-1-(1H-1,2,4-triazol-1-ylmethyl)naphthalene, (1R*,2R*)-6-fluoro-2-(4-fluorophenyl)-1,2,3,4-tetrahydro-1-(1H-imidazolylmethyl)naphthalene, (1R*,2R*)- and (1R*,2S*)-2-(4-fluorophenyl)-1,2,3,4-tetrahydro-1-(1H-1,2,4-triazol-1-ylmethyl)naphthalene-6-carbonitrile, (1R*,2R*)- and (1R*,2S*)-2-(4-fluorophenyl)-1,2,3,4-tetrahydro-1-(1H-imidazolylmethyl)naphthalene-6-carbonitrile, (1R*,2R*)- and (1R*,2S*)-1,2,3,4-tetrahydro-1-(1H-1,2, 4-triazol-1-ylmethyl)naphthalene-2,6-dicarbonitrile, (1R*,2R*)- and (1 R*,2S*)-1,2,3,4-tetrahydro-1-(1H-imidazol-1-ylmethyl)naphthalene-2,6-dicarbonitrile, (1 R*,2S*)-2-(4-fluorophenyl)-1,2,3,4-tetrahydro-1-(5-methyl-1H-imidazolylmethyl)naphthalene-6-carbonitrile, 2,2'-[5-(1H-1,2,4-triazol-1-ylmethyl)-1,3-phenylene] di(2-methylpropiononitrile), 2,2'-[5-(imidazol-1-ylmethyl)-1,3-phenylene]di(2-methylpropiononitrile), 2-[3-(1-hydroxy-1-methylethyl)-5-(5H-1,2,4-triazol-1-ylmethyl)phenyl]-2-methylpropiononitrile, 2,2'-[5-dideuterio(1H-1,2,4-triazol-1-yl)methyl-1,3-phenylene ]di(2-trideuteriomethyl-3,3,3-trideuteriopropiononitrile), 2,2'-[5-dideuterio(1H-1,2,4-triazol-1-yl)methyl-1,3-phenylene]di(2-methylpropiononitrile), (Z)-α-(1,2,4-triazol-1-ylmethyl)stilbene-4,4'-dicarbonitrile, (Z)-4'-chloro-a-(1,2,4-triazol-1-ylmethyl)stilbene-4-carbonitrile, (Z)-α-(1,2,4-triazol-1-yl methyl)-4'-(trifluoromethyl)stilbene-4-carbonitrile, (E)-β-fluoro-a-(1,2,4-triazol-1-ylmethyl)stilbene-4,4 '-dicarbonitrile, (Z)-4'-fluoro-a-(imidazol-1-ylmethyl)stilbene-4-carbonitrile, (Z)-2',4'-dichloro-a-(imidazol-1-ylmethyl)stilbene-4-carbonitrile, (Z)-4 '-chloro-a-(imidazol-1-ylmethyl)stilbene-4-carbonitrile, (Z)-α-(imidazol-1-ylmethyl)stilbene-4,4 '-dicarbonitrile, (Z)-α(5-methylimidazol-1-ylmethyl)stilbene-4,4'-dicarbonitrile, and (Z)-2-[2-(4-cyanophenyl)-3-(1,2,4-triazol-1-yl)propenyl] pyridine-5-carbonitrile.

19. A method according to claim 1, wherein the aromatase inhibitor is selected from the group consisting of 2-(4-chlorobenzyl)-2-fluoro-1,3-di(1,2,4-triazol-1-yl) propane, 2-fluoro-2-(2-fluoro-4-chlorobenzyl)-1,3-di(1,2,4-triazol-1-yl)propane,
2-fluoro-2-(2-fluoro-4-trifluoromethylbenzyl)-1,3-di(1,2,4-triazol-1-yl)propane,
3-(4-chlorophenyl)-1-(1,2,4-triazol-1-yl)-2-(1,2,4-triazol-1-ylmethyl)butan-2-ol,
2-(4-chloro-a-fluorobenzyl)-1,3-di(1,2,4-triazol-1-yl)propan-2-ol,
2-(4-chlorobenzyl)-1,3-bis(1,2,4-triazol-1-yl)propane,
4-[2-(4-chlorophenyl)-1,3-di(1,2,4-triazol-1-ylmethyl)ethoxymethyl]-benzonitrile,
1-(4-fluorobenzyl)-2-(2-fluoro-4-trifluoromethylphenyl)-1,3-di(1,2,4-triazol-1-yl)propan-2-ol,
2-(4-chlorophenyl)-1-(4-fluorophenoxy)-1,3-di(1,2,4-triazol-1-yl)propan-2-ol,
1-(4-cyanobenzyl)-2-(2,4-difluorophenyl)-1,3-di(1,2,4-triazol-1-yl)propan-2-ol,
2-(4-chlorophenyl)-1-phenyl-1,3-di(1,2,4-triazol-1-yl)propan-2-ol,
1,1-dimethyl-8-(1H-1,2,4-triazol-1-ylmethyl)-2(1H)-naphtho[2, 1-b]furanone,
1,2-dihydro-1,1-dimethyl-2-oxo-8-(1H-1,2,4-triazol-1-ylmethyl)naphtho[2, 1-b]furan-7-carbonitrile,
1,2-dihydro-1,1-dimethyl-2-oxo-8-(1 H-1,2,4-triazol-1-ylmethyl)naphtho[2,1-b]furan-7-carboxamide,
1,2-dihydro-1,1-dimethyl-2-oxo-8-[di(1 H-1,2,4-triazol-1-yl)methyl]naphtho[2,1-b]furan-7-carbonitrile,
4-[2-(4-cyanophenyl)-3-(1,2,4-triazol-1-yl)propyl]benzonitrile,
4-[1-(4-chlorobenzyl)-2-(1,2,4-triazol-1-yl)ethyl]benzonitrile,
4-[2-(1,2,4-triazol-1-yl)-1-(4-[trifluoromethyl]benzyl)ethyl]benzonitrile,
4-[2-(1,2,4-triazol-1-yl)-1-(4-[trifluoromethoxy]benzyl)ethyl]benzonitrile,
6-[2-(4-cyanophenyl)-3-(1,2,4-triazol-1-yl)-propyl]nicotinonitrile, and
4-[1-(1,2,4-triazol-1-yl-methyl)-2-(5-[trifluoromethyl]pyrid-2-yl)ethyl]benzonitrile.

20. A method according to claim 1, wherein the aromatase inhibitor is a steroidal aromatase inhibitor selected from the group consisting of
4-hydroxy-4-androstene-3,17-dione,
10-(2-propynyl)-oestr-4-ene-3,17-dione,
6-methyleneandrosta-1,4-diene-3,17-dione,
4-aminoandrosta-1,4,6-triene-3,17-dione, and
androsta-1,4,6-triene-3,17-dione.

* * * * *